United States Patent
Rajendran

(10) Patent No.: US 11,364,255 B2
(45) Date of Patent: Jun. 21, 2022

(54) THERAPEUTIC HERBAL COMPOSITIONS FOR IMPROVING JOINT HEALTH

(71) Applicant: Karallief, Inc., Cambridge, MA (US)

(72) Inventor: Krishna Rajendran, Allston, MA (US)

(73) Assignee: KARALLIEF, INC., Cambridge, MA (US)

( * ) Notice: Subject to any disclaimer, the term of this patent is extended or adjusted under 35 U.S.C. 154(b) by 0 days.

(21) Appl. No.: 16/946,721

(22) Filed: Jul. 1, 2020

(65) Prior Publication Data
US 2022/0000898 A1 Jan. 6, 2022

(51) Int. Cl.

| | |
|---|---|
| *A61K 36/82* | (2006.01) |
| *A61K 36/00* | (2006.01) |
| *A61K 31/7048* | (2006.01) |
| *A61P 19/02* | (2006.01) |
| *A61K 36/77* | (2006.01) |
| *A61K 36/899* | (2006.01) |
| *A61K 36/9066* | (2006.01) |
| *A61K 36/752* | (2006.01) |
| *A61K 36/324* | (2006.01) |
| *A61K 36/81* | (2006.01) |
| *A61K 36/87* | (2006.01) |
| *A61K 36/328* | (2006.01) |
| *A61K 36/39* | (2006.01) |
| *A61K 36/185* | (2006.01) |
| *A61K 36/42* | (2006.01) |
| *A61K 36/489* | (2006.01) |
| *A61K 36/53* | (2006.01) |

(52) U.S. Cl.
CPC ........ *A61K 31/7048* (2013.01); *A61K 36/185* (2013.01); *A61K 36/324* (2013.01); *A61K 36/328* (2013.01); *A61K 36/39* (2013.01); *A61K 36/42* (2013.01); *A61K 36/489* (2013.01); *A61K 36/53* (2013.01); *A61K 36/752* (2013.01); *A61K 36/77* (2013.01); *A61K 36/81* (2013.01); *A61K 36/82* (2013.01); *A61K 36/87* (2013.01); *A61K 36/899* (2013.01); *A61K 36/9066* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 2006/0141061 A1 | 6/2006 | Palpu et al. | |
| 2006/0246115 A1* | 11/2006 | Rueda | A23L 33/105 424/439 |
| 2016/0296582 A1* | 10/2016 | Kapadia | A61K 9/0014 |
| 2017/0136076 A1 | 5/2017 | Soman et al. | |
| 2017/0290875 A1* | 10/2017 | Gokaraju | A61K 9/0053 |
| 2020/0030349 A1* | 1/2020 | Schantl | A23L 33/105 |

FOREIGN PATENT DOCUMENTS

| | | | |
|---|---|---|---|
| CN | 105079479 A | | 11/2015 |
| CN | 108888776 A | * | 11/2018 |
| IN | DEL-2007-00851 A | | 2/2009 |
| IN | 201201544 I3 | * | 1/2013 |
| IN | 201201516 I3 | * | 1/2014 |
| IN | CHE-2012-01864 A | | 2/2015 |
| KR | 10-2016-0108574 A | | 9/2016 |
| KR | 2018221 B1 | * | 9/2019 |
| WO | WO2008/093355 A2 | | 8/2008 |

OTHER PUBLICATIONS

Aiyalu et al. ("Formulation and Evaluation of Novel Herbal Aerosol for Arthritis" Journal of Rhematology and arthritic Diseases, vol. 2, No. 4, pp. 1-12 (2017), Also see IDS (Year: 2017).*
Muniappann et al. ("Antiinflammatory and antiulcer activities of Bambusa arundinacea", Journal of EhnoPharmacology, 88 (2003) pp. 161-167) (Year: 2003).*
Ganesan ("Protective Effect of Withania somnifera and Cardiospermum halicacabum Extracts Against Collagenolytic Degradation of Collagen") Applied Biochemistry and Biotechnology 165, 1075-1091 (2011), (Year: 2011).*
Soni et al. ("Traditional uses, phytochemistry and pharmacological profile of Bambusa arudinacea Retz") TANG/www.e-tang.org 2013/vol. 3/Issue 3/e20 pp. 1-6) (Year: 2013).*
Aiyalu et al., "Formulation and Evaluation of Novel Herbal Aerosol for Arthritis," *J. of Rheumatology and Arthritic Diseases*, vol. 2, No. 4, pp. 1-12 (2017).
Aiyalu et al., "Formulation and Evaluation of Topical Herbal Gel for the Treatment of Arthritis in Animal Model," *Brazilian J. of Pharmaceutical Sciences*, vol. 52, No. 3., pp. 493-507 (2016).
Aiyalu et al., "Acute and Sub-Chronic Toxicity Study of Methanol Leaf Extract of Cardiospermum Halicacabum L and Vitex Negundo L in Rats," *Pharmacognosy Communications*, vol. 5, No. 1, pp. 39-45 (2015).
Aiyalu et al., "Evaluation of Synergistic Effect of Methanol Leaf Extract of Cardiospermum halicacabum and Vitex negundo on Inflammation and Arthritis," *J. of Herbs, Spices & Medicinal Plants*, vol. 20, No. 4, pp. 372-385 (2014).
Esakkimuthu, "Quantitative Analysis of Medicinal Plants Used to Treat Musculoskeletal Ailments by Non-Institutionally Trained Siddha Practitioners of Virudhunagar District, Tamil Nadu, India," *J. of Ayurveda and Integrative Medicine*, pp. 1-13 (2019).
PCT International Search Report and PCT Written Opinion for counterpart PCT International Application No. PCT/US2021/070723 dated Dec. 13, 2021, 15 pages.

(Continued)

*Primary Examiner* — Michael Barker
*Assistant Examiner* — Randall O Winston
(74) *Attorney, Agent, or Firm* — Finnegan, Henderson, Farabow, Garrett & Dunner, LLP

(57) ABSTRACT

Compositions including herbal extracts, such as a *Vitex negundo* extract, a *Cardiospermum halicacabum* extract, and a *Bambusa arundinacea* extract, and methods using such compositions are disclosed. For example, compositions and methods may be used to improve joint health.

34 Claims, 3 Drawing Sheets

(56) References Cited

OTHER PUBLICATIONS

Roy, S. K., et al., Analysis of Flavonoids and Iridoids in Vitex negundo by HPLC-PDA and Method Validation. Natural Products Communications. Sep. 2013, vol. 8, No. 9; pp. 1241-1244.

Menichini, F., et al., Chemical profiling and in vitro biological effects of Cardiospermum halicacabum L. (Sapindaceae) aerial parts and seeds for applications in neurodegenerative disorders, Journal of Enzyme Inhibition and Medicinal Chemistry, Oct. 2014, vol. 29, No. 5, pp. 677-685.

Rajendran, K., et al., Assessment of safety and efficacy of Karallief Easy ClimbTM, an herbal extract blend for supporting joint health: a double-blind, placebo-controlled, randomized clinical trial. International Journal of Basic and Clinical Pharmacology. Jan. 2021, vol. 10, No. 1; -pp. 1-9.

\* cited by examiner

THERAPEUTIC HERBAL COMPOSITIONS FOR IMPROVING JOINT HEALTH

The present disclosure relates generally to herbal compositions, dosage forms comprising such compositions, methods of improving joint health by administering such compositions, and methods for producing such compositions.

Osteoarthritis is a degenerative joint disease that affects the knees, hips, hands, feet, and spine. It is the most common form of arthritis, with more than 250 million people worldwide affected. It occurs most often in the elderly (people over the age of 65), women, and obese patients. Osteoarthritis of the knee is the most common.

Osteoarthritis is characterized by gradual loss of cartilage in movable joints due to abnormal remodeling of joint tissues following cell stress and extracellular matrix degradation. This causes narrowing of the joint space and chronic inflammation. Osteoarthritis is often initiated by micro- or macro-injury to the joint that result in bones rubbing together, creating pain, stiffness, crepitus, and impaired movement. It can also result from joint deterioration relating to age. The primary symptom of osteoarthritis is pain, which usually begins as intermittent weight-bearing pain that progresses to a more persistent, chronic pain.

The primary goal of treatment for osteoarthritis is to reduce symptoms and slow the progression of the disease. Many patients with osteoarthritis will have knee or hip replacements if the pain becomes unbearable or unmanageable with medication. Treatments that can manage pain and improve symptoms, functionality, and quality of life are highly sought after. Current osteoarthritis management techniques include non-pharmacologic approaches such as exercise, clinical devices, or weight management or pharmacologic approaches such as topical or oral non-steroidal anti-inflammatory drugs (NSAIDs) or acetaminophen. In some cases, where patients have severe pain that is not managed with over the counter (OTC) pain medications, opioids may be prescribed. Corticosteroid injections can also be used to reduce inflammation and improve knee mobility.

Many patients experiencing osteoarthritis are elderly and have comorbidities that may make it dangerous for them to take pain medications, such as NSAIDs, for an extended period of time. This is especially true in people who have cardiovascular or kidney disease, as NSAIDs contribute to the severity of these diseases. NSAIDs also pose a risk for serious gastrointestinal side effects including ulceration and bleeding. This makes the pain management of osteoarthritis difficult. Thus, there is a need for alternative approaches to improve joint health and alleviate or reduce the severity of the symptoms of osteoarthritis without the use of traditional pain medications such as NSAIDs.

The present disclosure addresses one or more of these needs by providing herbal compositions useful for improving joint health and reducing or alleviating at least one symptom of osteoarthritis, dosage forms comprising the herbal compositions, methods of administering the herbal compositions to a subject in need thereof, and methods of making the herbal compositions.

In one aspect, the present disclosure is directed to an herbal composition comprising a *Vitex negundo* extract and a *Cardiospermum halicacabum* extract. In some embodiments, the herbal composition further comprises a *Bambusa arundinacea* extract. In some embodiments, the herbal composition further comprises a *Citrus sinensis* extract. In some embodiments, the herbal composition further comprises a *Boswellia serrata* extract or a *Curcuma longa* extract. In some embodiments, the herbal composition further comprises a *Boswellia serrata* extract and a *Curcuma longa* extract. In some embodiments, the herbal composition does not comprise glucosamine.

In some embodiments, the herbal composition comprises from about 20% to about 40% of the *Vitex negundo* extract and from about 30% to about 50% of the *Cardiospermum halicacabum* extract, by weight relative to the total weight of the composition. In some embodiments, the composition further comprises from about 2% to about 10% of the *Bambusa arundinacea* extract, by weight relative to the total weight of the composition. In some embodiments, the composition further comprises from about 2% to about 10% of the *Citrus sinensis* extract, by weight relative to the total weight of the composition. In some embodiments, the composition further comprises from about 2% to about 10% of the *Boswellia serrata* extract and from about 10% to about 20% of the *Curcuma longa* extract, by weight relative to the total weight of the composition.

In some embodiments, the weight ratio of the *Vitex negundo* extract to the *Cardiospermum halicacabum* extract ranges from about 1:1 to about 1:2.5. In some embodiments, the weight ratio of the *Vitex negundo* extract to the *Cardiospermum halicacabum* extract ranges from about 1:1.1 to about 1:1.5.

In some embodiments, the composition further comprises a Green tea extract, a *Delonix elata* extract, an *Aesculus hippocastanum* extract, a *Citrus limon* extract, an Ashwagandha extract, a *Murraya koenigii* extract, a *Bacopa monnieri* extract, an *Evolvulus alsinoides* extract, a *Wrightia tinctoria* extract, a *Sophora japonica* extract, a *Cissus quadrangularis* extract, a *Commiphora mukul* extract, a *Terminalia arjuna* extract, a *Momordica charantia* extract, a *Phyllanthus niruri* extract, or an *Ocimum sanctum* extract, or any combination thereof. In some embodiments, the composition further comprises at least one pharmaceutically acceptable excipient or antioxidant. In some embodiments, the composition is a dietary supplement.

In some embodiments, the *Vitex negundo* extract comprises at least one iridoid glycoside. In some embodiments, the at least one iridoid glycoside is a compound according to Formula (I)

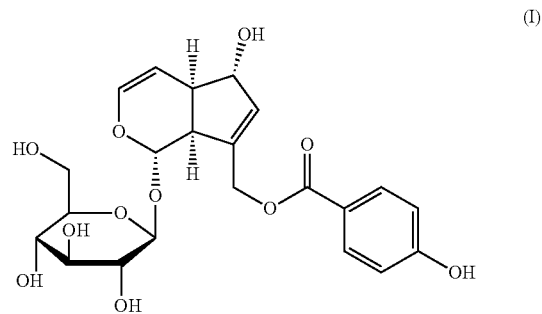

or a pharmaceutically acceptable salt or solvate thereof.

In some embodiments, the *Cardiospermum halicacabum* extract comprises at least one hydroxy flavone derivative. In some embodiments, the at least one hydroxy flavone derivative is a compound according to Formula (II)

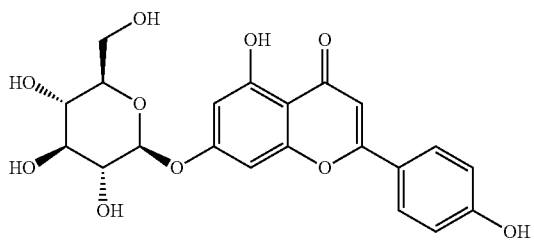
(II)

or a pharmaceutically acceptable salt or solvate thereof.

In another aspect, the present disclosure is directed to an herbal composition comprising a *Vitex negundo* extract, a *Cardiospermum halicacabum* extract, and glucosamine. In some embodiments, the composition further comprises a *Citrus sinensis* extract. In some embodiments, the composition further comprises a *Bambusa arundinacea* extract. In some embodiments, the composition further comprises a *Boswellia serrata* extract or a *Curcuma longa* extract. In some embodiments, the composition further comprises a *Boswellia serrata* extract and a *Curcuma longa* extract.

In some embodiments, the composition comprises from about 5% to about 20% of the *Vitex negundo* extract, from about 10% to about 30% of the *Cardiospermum halicacabum* extract, and from about 30% to about 50% of the glucosamine, by weight relative to the total weight of the composition. In some embodiments, the composition further comprises from about 2% to about 10% of the *Citrus sinensis* extract, by weight relative to the total weight of the composition. In some embodiments, the composition further comprises from about 2% to about 10% of the *Bambusa arundinacea* extract, by weight relative to the total weight of the composition. In some embodiments, the composition further comprises from about 2% to about 10% of a *Boswellia serrata* extract and from about 10% to about 20% of the *Curcuma longa* extract, by weight relative to the total weight of the composition.

In some embodiments, the weight ratio of the *Vitex negundo* extract to the *Cardiospermum halicacabum* extract ranges from about 1:1 to about 1:2.5. In some embodiments, the weight ratio of the *Vitex negundo* extract to the *Cardiospermum halicacabum* extract ranges from about 1:1.5 to about 1:2.5.

In some embodiments, the composition further comprises a Green tea extract, a *Delonix elata* extract, an *Aesculus hippocastanum* extract, a *Citrus limon* extract, an Ashwagandha extract, a *Murraya koenigii* extract, a *Bacopa monnieri* extract, an *Evolvulus alsinoides* extract, a *Wrightia tinctoria* extract, a *Sophora japonica* extract, a *Cissus quadrangularis* extract, a *Commiphora mukul* extract, a *Terminalia arjuna* extract, a *Momordica charantia* extract, a *Phyllanthus niruri* extract, or an *Ocimum sanctum* extract, or any combination thereof. In some embodiments, the composition further comprises at least one pharmaceutically acceptable excipient or antioxidant. In some embodiments, the composition is a dietary supplement.

In another aspect, the present disclosure is directed to a dosage form for oral or topical administration comprising an herbal composition according to the present disclosure. The herbal composition may be any of the herbal compositions according to the present disclosure.

In some embodiments, the dosage form is a dosage form for oral administration. In some embodiments, the dosage form is a capsule. In some embodiments, the capsule is a gelatin capsule, a polysaccharide capsule, or a vegetarian capsule. In some embodiments, the dosage form for oral administration comprises at least one pharmaceutically acceptable excipient.

In some embodiments, the dosage form for oral administration comprises from about 0.1 g to about 1.0 g of an herbal composition of the present disclosure. For example, in some embodiments, the dosage form for oral administration comprises about 0.5 g of an herbal composition of the present disclosure.

In some embodiments, the dosage form is a dosage form for topical administration. In some embodiments, the dosage form for topical administration may comprise an herbal composition according to the present disclosure and *Aloe vera*.

In another aspect, the present disclosure is directed to a method of improving joint health in a subject, comprising administering an herbal composition of the present disclosure to the subject. The herbal composition may be any herbal composition according to the present disclosure.

In some embodiments, the subject is a mammal. In some embodiments, the subject is a human. In some embodiments, the subject has osteoarthritis. In some embodiments, the osteoarthritis is knee osteoarthritis.

In some embodiments, the herbal composition of the present disclosure is administered orally. In some embodiments, the oral daily dosage of the herbal composition ranges from about 0.1 g to about 4 g. For example, in some embodiments, the daily dosage is about 1 g per day orally. In some embodiments, the herbal composition is administered twice per day orally. For example, in some embodiments, about 0.5 g of the herbal composition is administered orally twice per day, for a total daily dosage of about 1.0 g per day.

In another aspect, the present disclosure is directed to a method of making an herbal composition comprising extracting *Vitex negundo* aerial parts to form a *Vitex negundo* extract; extracting *Cardiospermum halicacabum* aerial parts to form a *Cardiospermum halicacabum* extract; combining the *Vitex negundo* extract and the *Cardiospermum halicacabum* extract; and blending the combined extracts. In some embodiments, the method further comprises: extracting *Citrus sinensis* peels to form a *Citrus sinensis* extract, extracting *Bambusa arundinacea* shoots to form a *Bambusa arundinacea* extract, extracting *Boswellia serrata* resin to form a *Boswellia serrata* extract, and extracting *Curcuma longa* rhizomes to form a *Curcuma longa* extract; combining the *Citrus sinensis* extract, the *Bambusa arundinacea* extract, the *Boswellia serrata* extract, and the *Curcuma longa* extract with the *Vitex negundo* extract and the *Cardiospermum halicacabum* extract; and blending the combined extracts.

Figure 1:
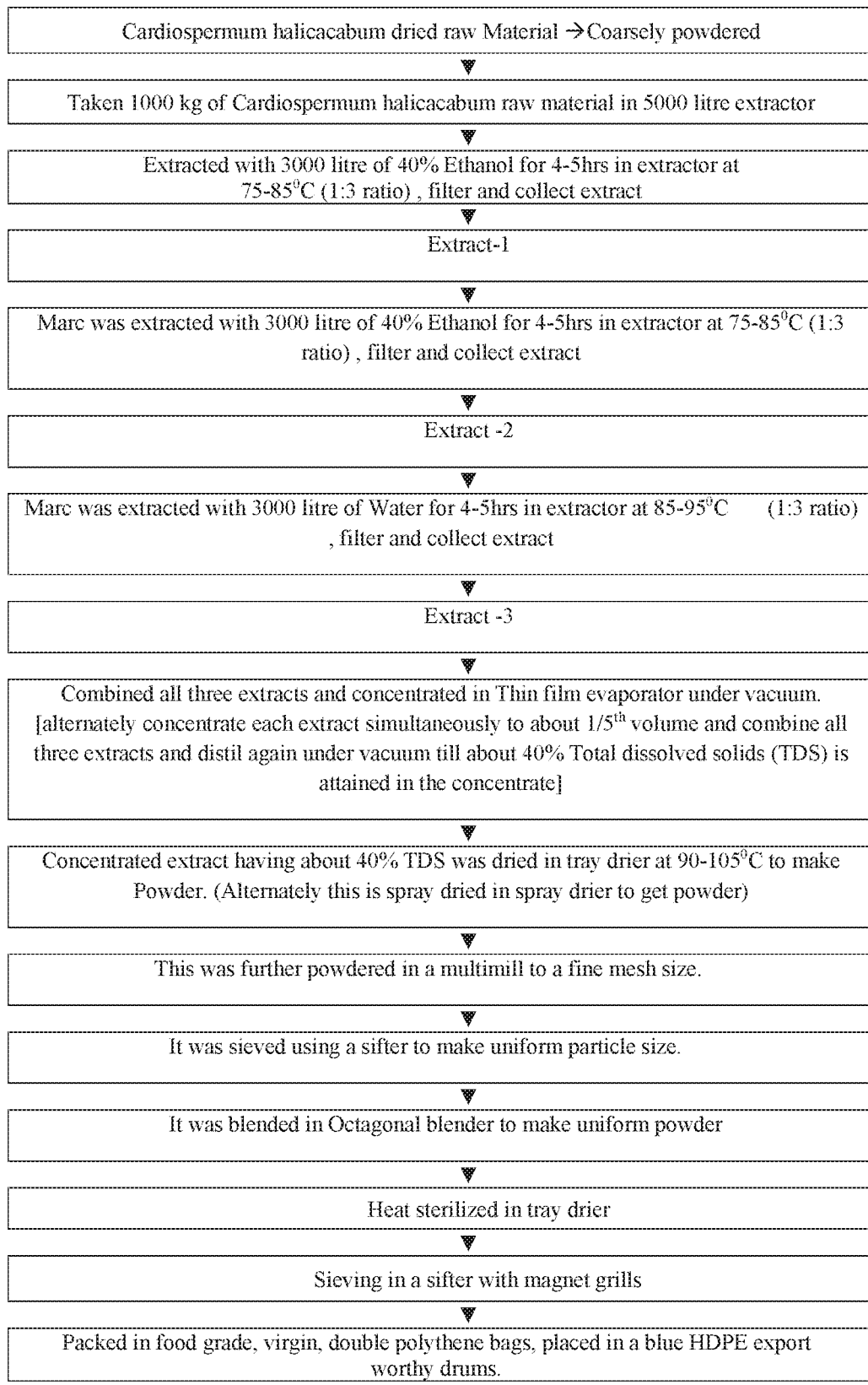
FIG. 1 illustrates an exemplary process for producing a *Cardiospermum halicacabum* extract according to the present disclosure.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

As used herein, "a" or "an" entity refers to one or more of that entity. As such, the terms "a" (or "an"), "one or more", and "at least one" are used interchangeably herein.

As used herein, the term "reduce" indicates a lessening or decrease of an indicated value relative to a reference value. In some embodiments, the term "reduce" (including "reduction") refers to a lessening or a decrease of an indicated value by about 5%, 10%, 15%, 20%, 25%, 30%, 35%, 40%, 45%, or 50% relative to a reference value. Unless indicated otherwise, percentage (%) of ingredients refer to total % by weight typically on a dry weight basis unless otherwise indicated.

As used herein, the term "concentrating" refers to an operation that aims to increase the concentration of the desired component, especially by removing extraction solvent. The term also encompasses the operation of drying an extract so as to remove all or almost all of the aqueous solvent (and endogenous water) contained therein.

The present disclosure is directed to herbal compositions comprising at least one herbal extract. The present disclosure is also directed to dosage forms comprising herbal compositions. The present disclosure is also directed to methods of improving joint health and/or reducing or alleviating at least one symptom of osteoarthritis comprising administering an herbal composition to a subject in need thereof. The present disclosure is also directed to methods of making herbal compositions.

The herbal compositions of the present disclosure comprise at least one herbal extract. In some embodiments, the at least one herbal extract is chosen from a *Vitex negundo* extract, a *Cardiospermum halicacabum* extract, a *Citrus sinensis* extract, a *Bambusa arundinacea* extract, a *Boswellia serrata* extract, a *Curcuma longa* extract, and combinations thereof.

In some embodiments of the present disclosure, the herbal composition comprises a *Vitex negundo* extract. In some embodiments, the *Vitex negundo* extract is an extract of *Vitex negundo* aerial parts. In some embodiments, the *Vitex negundo* aerial parts comprise *Vitex negundo* leaves. In some embodiments, the *Vitex negundo* aerial parts do not comprise sticks and stems.

In some embodiments, the *Vitex negundo* is dried and powdered before extraction. In some embodiments, the *Vitex negundo* is extracted with an extraction solvent chosen from water, alcohol, and combinations thereof. In some embodiments, the extraction solvent is water. In some embodiments, the extraction solvent is an aqueous alcohol, such as aqueous ethanol, such as, for example, 40% ethanol in water (v/v). In some embodiments, the weight ratio of *Vitex negundo* to extraction solvent is about 1:3. In some embodiments, the *Vitex negundo* is extracted at an elevated temperature, such as, for example, from about 75° C. to 85° C. The *Vitex negundo* may be extracted more than once, such as three times, and the extracts may be combined and distilled. The distilled *Vitex negundo* extracts may be dried and further powdered to a fine mesh size. The powdered *Vitex negundo* extracts may be heat sterilized and sieved.

In some embodiments, the *Vitex negundo* extract comprises at least one iridoid glycoside, such as, e.g., [(1S,4aR,5S,7aS)-5-Hydroxy-1-[(2S,3R,4S,5S,6R)-3,4,5-trihydroxy-6-(hydroxymethyl)oxan-2-yl]oxy-1,4a,5,7a-tetrahydrocyclopenta[c]pyran-7-yl]methyl 4-hydroxybenzoate or a pharmaceutically acceptable salt or solvate thereof. In some embodiments, the at least one iridoid glycoside is a compound according to Formula (I)

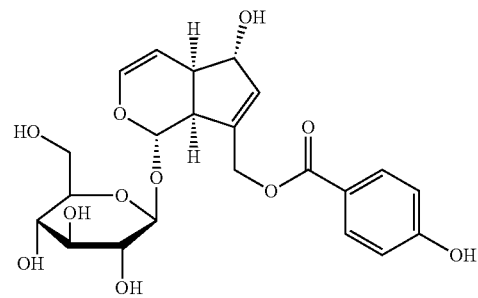

(I)

or a pharmaceutically acceptable salt or solvate thereof. Without being bound by theory, the *Vitex negundo* extracts of the present disclosure, such as, for example, *Vitex negundo* extracts comprising at least one iridoid glycoside such as the compound according to Formula (I) or the pharmaceutically acceptable salt or solvate thereof, may improve joint health and/or reduce or alleviate at least one symptom of osteoarthritis when administered to a subject by increasing secretions of synovial fluid in the subject's joints and reducing joint pain.

In some embodiments of the present disclosure, the herbal composition comprises from about 5% to about 40% of the *Vitex negundo* extract, by weight relative to the total weight of the herbal composition. For example, in some embodiments, the herbal composition comprises from about 20% to about 40% of the *Vitex negundo* extract, such as from about 25% to about 40%, from about 29% to about 40%, from about 20% to about 35%, from about 25% to about 35%, or from about 29% to about 35% of the *Vitex negundo* extract, by weight relative to the total weight of the herbal composition. In some embodiments, the herbal composition comprises about 32% of the *Vitex negundo* extract, by weight relative to the total weight of the herbal composition. In other embodiments of the present disclosure, the herbal composition comprises from about 5% to about 20% of the *Vitex negundo* extract, such as from about 5% to about 15%, from about 5% to about 12%, from about 8% to about 20%, from about 8% to about 15%, or from about 8% to about 12% of the *Vitex negundo* extract, by weight relative to the total weight of the herbal composition. In some embodiments, the herbal composition comprises about 10% of the *Vitex negundo* extract, by weight relative to the total weight of the herbal composition.

In some embodiments of the present disclosure, the herbal composition comprises a *Cardiospermum halicacabum* extract. In some embodiments, the *Cardiospermum halicacabum* extract is an extract of *Cardiospermum halicacabum* root parts. In some embodiments, the *Cardiospermum halicacabum* extract is an extract of *Cardiospermum halicacabum* aerial parts. In some embodiments, the *Cardiospermum halicacabum* aerial parts comprise *Cardiospermum halicacabum* leaves and stems. In some embodiments, the *Cardiospermum halicacabum* aerial parts comprise *Cardiospermum halicacabum* leaves. In some embodiments, the *Cardiospermum halicacabum* aerial parts comprise *Cardiospermum halicacabum* stems.

In some embodiments, the *Cardiospermum halicacabum* is dried and powdered before extraction. In some embodiments, the *Cardiospermum halicacabum* is extracted with an extraction solvent chosen from water, alcohol, and combinations thereof. In some embodiments, the extraction solvent is water. In some embodiments, the extraction solvent is an aqueous alcohol, such as aqueous ethanol, such as, for example, 40% ethanol in water (v/v). In some embodiments, the weight ratio of *Cardiospermum halicacabum* to extraction solvent is about 1:3. In some embodiments, the *Cardiospermum halicacabum* is extracted at an elevated temperature, such as, for example, from about 75° C. to 85° C. The *Cardiospermum halicacabum* may be extracted more than once, such as three times, and the extracts may be combined and distilled. The distilled *Cardiospermum halicacabum* extracts may be dried and further powdered to a fine mesh size. The powdered *Cardiospermum halicacabum* extracts may be heat sterilized and sieved.

In some embodiments, the *Cardiospermum halicacabum* extract comprises at least one hydroxy flavone derivative, such as, for example, 5-hydroxy-2-(4-hydroxyphenyl)-7-[3,4,5-trihydroxy-6-(hydroxymethyl)oxan-2-yl]oxychromen-4-one or a pharmaceutically acceptable salt or solvate thereof. In some embodiments, the at least one hydroxy flavone derivative is a compound according to Formula (II)

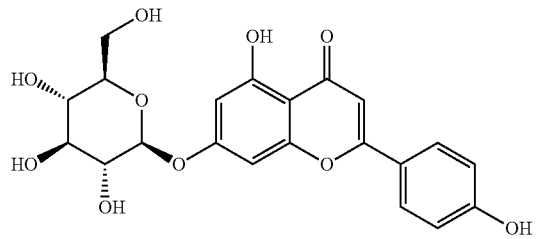

(II)

or a pharmaceutically acceptable salt or solvate thereof. Without being bound by theory, the *Cardiospermum halicacabum* extracts of the present disclosure, such as, for example, *Cardiospermum halicacabum* extracts comprising at least one hydroxy flavone derivative such as the compound according to Formula (II) or a pharmaceutically acceptable salt or solvate thereof, may improve joint health and/or reduce or alleviate at least one symptom of osteoarthritis when administered to a subject in need thereof by regenerating the cartilage and ligaments of the subject's joints and reducing joint pain.

In some embodiments of the present disclosure, the herbal composition comprises from about 10% to about 50% of the *Cardiospermum halicacabum* extract, by weight relative to the total weight of the composition. For example, in some embodiments, the herbal composition comprises from about 30% to about 50% of the *Cardiospermum halicacabum* extract, such as from about 30% to about 45%, from about 30% to about 40%, from about 34% to about 50%, from about 34% to about 45%, or from about 34% to about 40% of the *Cardiospermum halicacabum* extract, by weight relative to the total weight of the herbal composition. In some embodiments, the herbal composition comprises about 37% of the *Cardiospermum halicacabum* extract, by weight relative to the total weight of the herbal composition. In other embodiments, the herbal composition comprises from about 10% to about 30% of the *Cardiospermum halicacabum* extract, such as from about 15% to about 30%, from about 15% to about 25%, from about 15% to about 22%, from about 18% to about 30%, from about 18% to about 25%, or from about 18% to about 22% of the *Cardiospermum halicacabum* extract, by weight relative to the total weight of the herbal composition. In some embodiments, the herbal composition comprises about 20% of the *Cardiospermum halicacabum* extract, by weight relative to the total weight of the herbal composition.

In some embodiments of the present disclosure, the herbal composition comprises a *Citrus sinensis* extract. In some embodiments, the *Citrus sinensis* extract is an extract of *Citrus sinensis* roots. In some embodiments, the *Citrus sinensis* extract is an extract of *Citrus sinensis* aerial parts, such as *Citrus sinensis* fruits, *Citrus sinensis* leaves, *Citrus sinensis* peels, or any combination thereof. In some embodiments, the *Citrus sinensis* aerial parts comprise *Citrus sinensis* peels.

In some embodiments, the *Citrus sinensis* is dried and powdered before extraction. In some embodiments, the *Citrus sinensis* is extracted with an extraction solvent chosen from water, alcohol, and combinations thereof. In some embodiments, the extraction solvent is water. In some embodiments, the extraction solvent is an aqueous alcohol, such as aqueous ethanol, such as, for example, 40% ethanol in water (v/v). In some embodiments, the weight ratio of *Citrus sinensis* to extraction solvent is about 1:3. In some embodiments, the *Citrus sinensis* is extracted at an elevated temperature, such as, for example, from about 75° C. to 85° C. The *Citrus sinensis* may be extracted more than once, such as three times, and the extracts may be combined and distilled. The distilled *Citrus sinensis* extracts may be dried and further powdered to a fine mesh size. The powdered *Citrus sinensis* extracts may be heat sterilized and sieved.

In some embodiments, the *Citrus sinensis* extract comprises at least one *citrus* bioflavonoid. In some embodiments, the at least one *citrus* bioflavonoid is chosen from Hesperidin, Diosmin, Naringenin, Naringin, Quercetin, Rutin, and Kaempferol, including combinations and pharmaceutically acceptable salts and solvates thereof. Without being bound by theory, the *Citrus sinensis* extracts of the present disclosure, such as, for example, *Citrus sinensis* extracts comprising at least one of the aforementioned *citrus* bioflavonoids, may improve joint health and/or reduce or alleviate at least one symptom of osteoarthritis when administered to a subject by increasing blood flow to the subject's joints.

In some embodiments of the present disclosure, the herbal composition comprises from about 2% to about 10% of the *Citrus sinensis* extract, by weight relative to the total weight of the herbal composition. For example, in some embodiments, the herbal composition comprises from about 2% to about 8% of the *Citrus sinensis* extract, such as from about 2% to about 6%, from about 3% to about 8%, or from about 3% to about 6% of the *Citrus sinensis* extract, by weight relative to the total weight of the herbal composition. In some embodiments, the herbal composition comprises about 5% of the *Citrus sinensis* extract, by weight relative to the total weight of the herbal composition. In some embodiments, the herbal composition comprises about 4% of the *Citrus sinensis* extract, by weight relative to the total weight of the herbal composition.

In some embodiments of the present disclosure, the herbal composition comprises a *Bambusa arundinacea* extract. In some embodiments, the *Bambusa arundinacea* extract is an extract of the deposits of shoots of *Bambusa arundinacea*. In some embodiments, the *Bambusa arundinacea* extract is an extract of *Bambusa arundinacea* shoots.

In some embodiments, the *Bambusa arundinacea* is dried and powdered before extraction. In some embodiments, the *Bambusa arundinacea* is extracted with an extraction solvent chosen from water, alcohol, and combinations thereof. In some embodiments, the extraction solvent is water. In some embodiments, the water is acidified with at least one acid. In some embodiments, the extraction solvent is an aqueous alcohol, such as aqueous ethanol, such as, for example, 40% ethanol in water (v/v). In some embodiments, the aqueous alcohol is acidified with at least one acid. In some embodiments, the weight ratio of *Bambusa arundinacea* to extraction solvent is about 1:3. In some embodiments, the *Bambusa arundinacea* is extracted at an elevated temperature, such as, for example, from about 75° C. to 85° C. The *Bambusa arundinacea* may be extracted more than once, such as three times, and the extracts may be combined and distilled. The distilled *Bambusa arundinacea* extracts may be dried and further powdered to a fine mesh size. The powdered *Bambusa arundinacea* extracts may be heat sterilized and sieved.

In some embodiments, the *Bambusa arundinacea* extract comprises silica. For example, in some embodiments, the *Bambusa arundinacea* extract comprises at least about 50% silica, by weight relative to the total weight of the extract, such as at least about 60%, at least about 65%, at least about 70%, or at least about 75% silica by weight relative to the total weight of the extract. Without being bound by theory, the *Bambusa arundinacea* extracts of the present disclosure, such as, for example, *Bambusa arundinacea* extracts comprising at least about 50% silica by weight, may improve joint health and/or reduce or alleviate at least one symptom of osteoarthritis when administered to a subject by strengthening the subject's bones.

In some embodiments of the present disclosure, the herbal composition comprises from about 2% to about 10% of the *Bambusa arundinacea* extract, by weight relative to the total weight of the herbal composition. For example, in some embodiments, the herbal composition comprises from about 2% to about 8% of the *Bambusa arundinacea* extract, such as from about 2% to about 6%, from about 4% to about 8%, or from about 4% to about 6% of the *Bambusa arundinacea* extract, by weight relative to the total weight of the herbal composition. In some embodiments, the herbal composition comprises about 5% of the *Bambusa arundinacea* extract, by weight relative to the total weight of the herbal composition.

In some embodiments of the present disclosure, the herbal composition comprises a *Boswellia serrata* extract. In some embodiments, the *Boswellia serrata* extract is an extract of *Boswellia serrata* aerial parts. In some embodiments, the *Boswellia serrata* extract is an extract of *Boswellia serrata* gum resins.

In some embodiments, the *Boswellia serrata* is dried and powdered before extraction. In some embodiments, the *Boswellia serrata* is washed with n-hexane before extraction. In some embodiments, the *Boswellia serrata* is extracted with an extraction solvent chosen from water, alcohol, and combinations thereof. In some embodiments, the extraction solvent is water. In some embodiments, the extraction solvent is an aqueous alcohol, such as aqueous ethanol, such as, for example, 40% ethanol in water (v/v). In some embodiments, the weight ratio of *Boswellia serrata* to extraction solvent is about 1:3. In some embodiments, the *Boswellia serrata* is extracted at an elevated temperature, such as, for example, from about 75° C. to 85° C. The *Boswellia serrata* may be extracted more than once, such as three times, and the extracts may be combined and distilled. The distilled *Boswellia serrata* extracts may be dried and further powdered to a fine mesh size. The powdered *Boswellia serrata* extracts may be heat sterilized and sieved.

In some embodiments, the *Boswellia serrata* extract comprises at least one compound chosen from monoterpenes, diterpenes, triterpenes, tetracyclic triterpenic acids, derivatives thereof, including pharmaceutically acceptable salts and solvates thereof, and combinations thereof. In some embodiments, the *Boswellia serrata* extract comprises at least one pentacyclic triterpenic acid. In some embodiments, the at least one pentacyclic triterpenic acid is chosen from β-boswellic acid, acetyl-3-boswellic acid, 11-keto-β-boswellic acid, acetyl-11-keto-β-boswellic acid, derivatives thereof, including pharmaceutically acceptable salts and solvates thereof, and combinations thereof.

In some embodiments, the *Boswellia serrata* extract comprises (3R,4R,4aR,6aR,6bS,8aR,12aR,14aR,14bR)-3-hydroxy-4,6a,6b,8a,11,11,14b-heptamethyl-1,2,3,4a,5,6,7,8,9,10,12,12a,14,14a-tetradecahydropicene-4-carboxylic acid, which has the following chemical structure:

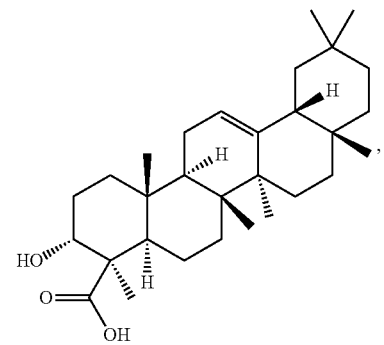

or a pharmaceutically acceptable salt or solvate thereof.

In some embodiments, the *Boswellia serrata* extract comprises (3R,4R,4aR,6aR,6bS,8aR,11R,12S,12aR,14aR,14bR)-3-hydroxy-4,6a,6b,8a,11,12,14b-heptamethyl-2,3,4a,5,6,7,8,9,10,11,12,12a,14,14a-tetradecahydro-1H-picene-4-carboxylic acid, which has the following chemical structure:

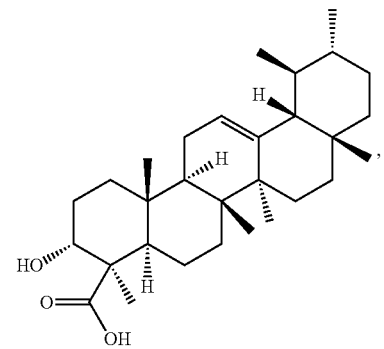

or a pharmaceutically acceptable salt or solvate thereof.

In some embodiments, the *Boswellia serrata* extract comprises (3R,4R,4aR,6aR,6bS,8aR,11R,12S,12aR,14aR,14bS)-3-hydroxy-4,6a,6b,8a,11,12,14b-heptamethyl-14-oxo-1,2,3,4a,5,6,7,8,9,10,11,12,12a,14a-tetradecahydropicene-4-carboxylic acid, which has the following chemical structure:

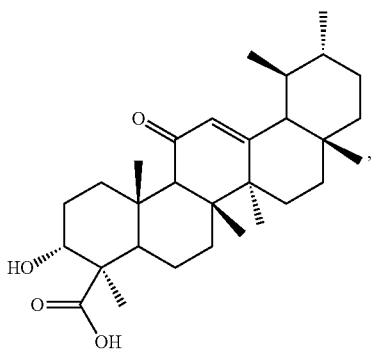 [SMILES: C[C@@H]1CC[C@]2(C)CC[C@]3(C)C(=CC(=O)C4[C@@]5(C)CC[C@@H](O)[C@](C)(C(=O)O)C5CC[C@]43C)C2[C@H]1C]

or a pharmaceutically acceptable salt or solvate thereof.

In some embodiments of the present disclosure, the herbal composition comprises from about 2% to about 10% of the *Boswellia serrata* extract, by weight relative to the total weight of the herbal composition. For example, in some embodiments, the herbal composition comprises from about 2% to about 8% of the *Boswellia serrata* extract, such as from about 2% to about 6%, from about 4% to about 8%, or from about 4% to about 6% of the *Boswellia serrata* extract, by weight relative to the total weight of the herbal composition. In some embodiments, the herbal composition comprises about 5% of the *Boswellia serrata* extract, by weight relative to the total weight of the herbal composition.

In some embodiments of the present disclosure, the herbal composition comprises a *Curcuma longa* extract. In some embodiments, the *Curcuma longa* extract is an extract of *Curcuma longa* shoots. In some embodiments, the *Curcuma longa* extract is an extract of *Curcuma longa* roots. In some embodiments, the *Curcuma longa* extract is an extract of *Curcuma longa* rhizomes.

In some embodiments, the *Curcuma longa* is dried and powdered before extraction. In some embodiments, the *Curcuma longa* is extracted with an extraction solvent chosen from water, alcohol, and combinations thereof. In some embodiments, the extraction solvent is water. In some embodiments, the extraction solvent is an aqueous alcohol, such as aqueous ethanol, such as, for example, 40% ethanol in water (v/v). In some embodiments, the weight ratio of *Curcuma longa* to extraction solvent is about 1:3. In some embodiments, the *Curcuma longa* is extracted at an elevated temperature, such as, for example, from about 75° C. to 85° C. The *Curcuma longa* may be extracted more than once, such as three times, and the extracts may be combined and distilled. The distilled *Curcuma longa* extracts may be dried and further powdered to a fine mesh size. The powdered *Curcuma longa* extracts may be heat sterilized and sieved.

In some embodiments, the *Curcuma longa* extract comprises at least one saponin glycoside or a pharmaceutically acceptable salt or solvate thereof. In some embodiments, the at least one saponin glycoside, salt, or solvate thereof is water soluble.

In some embodiments of the present disclosure, the herbal composition comprises from about 5% to about 25% of the *Curcuma longa* extract, by weight relative to the total weight of the herbal composition. For example, in some embodiments, the herbal composition comprises from about 10% to about 20% of the *Curcuma longa* extract, such as from about 12% to about 20%, from about 10% to about 18%, or from about 12% to about 18% of the *Curcuma longa* extract, by weight relative to the total weight of the herbal composition. In some embodiments, the herbal composition comprises about 15% of the *Curcuma longa* extract, by weight relative to the total weight of the herbal composition.

In some embodiments of the present disclosure, the herbal composition comprises glucosamine, which is (3R,4R,5S)-3-Amino-6-(hydroxymethyl)oxane-2,4,5-triol, or a derivative thereof, such as a pharmaceutically acceptable salt or solvate thereof. In some embodiments, the glucosamine is chosen from glucosamine sulfate, glucosamine hydrochloride, n-acetylglucosamine, glucosamine sulfate potassium chloride, glucosamine sulfate sodium chloride, vegetarian glucosamine, and combinations thereof. In some embodiments, the glucosamine is glucosamine sulfate.

Glucosamine may improve joint health by helping to rebuild the cartilage and fluid surrounding joints and/or by helping to prevent the breakdown of these substances. However, at the high doses found in conventional osteoarthritis supplements (e.g., 1000 to 1500 mg/day), glucosamine commonly causes side effects such as nausea, heartburn, diarrhea, and constipation, which may lead to discontinuation of conventional, high-dose glucosamine supplementation. The herbal compositions of the present disclosure avoid these side effects by providing a relatively low dose of glucosamine (e.g., about 400 mg/day) in combination with the potent herbal extracts of the present disclosure, or by not comprising glucosamine at all. Thus, the herbal compositions of the present disclosure may be taken for extended periods of time, or indefinitely, without the unpleasant side effects that may lead to discontinuation of conventional high-dose glucosamine supplements.

In some embodiments of the present disclosure, the herbal composition comprises from about 30% to about 50% glucosamine, such as from about 30% to about 45%, from about 35% to about 50%, from about 35% to about 45%, from about 35% to about 43%, or from about 37% to about 43% glucosamine, by weight relative to the total weight of the herbal composition. In some embodiments, the herbal composition comprises about 40% glucosamine, by weight relative to the total weight of the herbal composition.

In a first aspect, the present disclosure is directed to an herbal composition comprising a *Vitex negundo* extract and a *Cardiospermum halicacabum* extract. In some embodiments, the herbal composition comprises from about 5% to about 40% of the *Vitex negundo* extract and from about 10% to about 50% of the *Cardiospermum halicacabum* extract, by weight relative to the total weight of the herbal composition. In some embodiments, the herbal composition consists essentially of the *Vitex negundo* extract and the *Cardiospermum halicacabum* extract. In some embodiments, the herbal composition consists of the *Vitex negundo* extract, the *Cardiospermum halicacabum* extract, and, optionally, at least one pharmaceutically acceptable excipient.

In some embodiments of the first aspect, the herbal composition comprises a relatively high concentration of the *Vitex negundo* extract and the *Cardiospermum halicacabum* extract. For example, in some embodiments, the herbal composition comprises at least about 20% of the *Vitex negundo* extract, such as at least about 25%, at least about 30%, or at least about 32% of the *Vitex negundo* extract, by weight relative to the total weight of the herbal composition. In some embodiments, the herbal composition comprises at least about 20% of the *Cardiospermum halicacabum* extract, such as at least about 25%, at least about 30%, at least about 35%, or at least about 37% of the *Cardiospermum halicacabum* extract, by weight relative to the total weight of the herbal composition. In some embodiments, the *Vitex negundo* extract and the *Cardiospermum halicacabum* extract together comprise at least about 40% of the total weight of the herbal composition, such as at least about 50%, at least about 60%, at least about 65%, or at least about 70% of the total weight of the herbal composition.

In some embodiments of the first aspect, the herbal composition comprises from about 20% to about 40% of the *Vitex negundo* extract, such as from about 25% to about 40%, from about 29% to about 40%, from about 20% to about 35%, from about 25% to about 35%, or from about 29% to about 35% of the *Vitex negundo* extract, by weight relative to the total weight of the composition. In some embodiments, the herbal composition comprises about 32% of the *Vitex negundo* extract, by weight relative to the total weight of the composition.

In some embodiments of the first aspect, the herbal composition comprises from about 30% to about 50% of the *Cardiospermum halicacabum* extract, such as from about 30% to about 45%, from about 30% to about 40%, from about 34% to about 50%, from about 34% to about 45%, or from about 34% to about 40% of the *Cardiospermum halicacabum* extract, by weight relative to the total weight of the herbal composition. In some embodiments, the herbal composition comprises about 37% of the *Cardiospermum halicacabum* extract, by weight relative to the total weight of the herbal composition.

In other embodiments of the first aspect, the herbal composition comprises a lower concentration of the *Vitex negundo* extract and the *Cardiospermum halicacabum* extract. For example, in some embodiments, the herbal composition comprises from about 5% to about 20% of the *Vitex negundo* extract, such as from about 5% to about 15%, from about 5% to about 12%, from about 8% to about 20%, from about 8% to about 15%, or from about 8% to about 12% of the *Vitex negundo* extract, by weight relative to the total weight of the herbal composition. In some embodiments, the herbal composition comprises about 10% of the *Vitex negundo* extract, by weight relative to the total weight of the herbal composition. In some embodiments, the herbal composition comprises from about 10% to about 30% of the *Cardiospermum halicacabum* extract, such as from about 15% to about 30%, from about 15% to about 25%, from about 15% to about 22%, from about 18% to about 30%, from about 18% to about 25%, or from about 18% to about 22% of the *Cardiospermum halicacabum* extract, by weight relative to the total weight of the herbal composition. In some embodiments, the herbal composition comprises about 20% of the *Cardiospermum halicacabum* extract, by weight relative to the total weight of the herbal composition.

In some embodiments of the first aspect, the weight ratio of the *Vitex negundo* extract to the *Cardiospermum halicacabum* extract ranges from about 1.2:1 to about 1:3, such as from about 1.2:1 to about 1:2.5, from about 1:1 to about 1:3, or from about 1:1 to about 1:2.5. For example, in some embodiments of the first aspect, the weight ratio of the *Vitex negundo* extract to the *Cardiospermum halicacabum* extract ranges from about 1.2:1 to about 1:2, from about 1.2:1 to about 1:1.5, from about 1.2:1 to about 1:1.2, from about 1:1 to about 1:2, from about 1:1 to about 1:1.5, from about 1:1 to about 1:1.2, from about 1:1.1 to about 1:2, from about 1:1.1 to about 1:1.5, or from about 1:1.1 to about 1:1.2. In other embodiments of the first aspect, the weight ratio of the *Vitex negundo* extract to the *Cardiospermum halicacabum* extract ranges from about 1:1.5 to about 1:3, from about 1:1.5 to about 1:2.5, from about 1:1.5 to about 1:2.2, from about 1:1.7 to about 1:3, from about 1:1.7 to about 1:2.5, from about 1:1.7 to about 1:2.2, from about 1:2 to about 1:3, from about 1:2 to about 1:2.5, or from about 1:2 to about 1:2.2.

In some embodiments of the first aspect, the herbal composition further comprises a *Citrus sinensis* extract. For example, in some embodiments, the herbal composition comprises a *Vitex negundo* extract, a *Cardiospermum halicacabum* extract, and a *Citrus sinensis* extract. In some embodiments, the herbal composition consists essentially of the *Vitex negundo* extract, the *Cardiospermum halicacabum* extract, and the *Citrus sinensis* extract. In some embodiments, the herbal composition consists of the *Vitex negundo* extract, the *Cardiospermum halicacabum* extract, the *Citrus sinensis* extract, and, optionally, at least one pharmaceutically acceptable excipient.

In some embodiments of the first aspect, the herbal composition comprises from about 2% to about 10% of the *Citrus sinensis* extract, by weight relative to the total weight of the herbal composition, such as from about 2% to about 8%, from about 2% to about 6%, from about 3% to about 8%, or from about 3% to about 6% of the *Citrus sinensis* extract, by weight relative to the total weight of the herbal composition. In some embodiments, the herbal composition comprises about 5% of the *Citrus sinensis* extract, by weight relative to the total weight of the herbal composition.

For example, in some embodiments of the first aspect, the herbal composition comprises from about 20% to about 40% of the *Vitex negundo* extract, from about 30% to about 50% of the *Cardiospermum halicacabum* extract, and from about 2% to about 10% of the *Citrus sinensis* extract, by weight relative to the total weight of the herbal composition. For example, in some embodiments, the herbal composition comprises from about 29% to about 35% of the *Vitex negundo* extract, from about 34% to about 40% of the *Cardiospermum halicacabum* extract, and from about 3% to about 6% of the *Citrus sinensis* extract, by weight relative to the total weight of the herbal composition.

In some embodiments of the first aspect, the herbal composition further comprises a *Bambusa arundinacea* extract. For example, in some embodiments, the herbal composition comprises a *Vitex negundo* extract, a *Cardiospermum halicacabum* extract, and a *Bambusa arundinacea* extract. In some embodiments, the herbal composition consists essentially of the *Vitex negundo* extract, the *Cardiospermum halicacabum* extract, and the *Bambusa arundinacea* extract. In some embodiments, the herbal composition consists of the *Vitex negundo* extract, the *Cardiospermum halicacabum* extract, the *Bambusa arundinacea* extract, and, optionally, at least one pharmaceutically acceptable excipient.

In some embodiments of the first aspect, the herbal composition comprises from about 2% to about 10% of the *Bambusa arundinacea* extract, by weight relative to the total weight of the herbal composition, such as from about 2% to about 8%, from about 2% to about 6%, from about 4% to about 8%, or from about 4% to about 6% of the *Bambusa arundinacea* extract, by weight relative to the total weight of the herbal composition. In some embodiments, the herbal composition comprises about 5% of the *Bambusa arundinacea* extract, by weight relative to the total weight of the herbal composition.

For example, in some embodiments of the first aspect, the herbal composition comprises from about 20% to about 40% of the *Vitex negundo* extract, from about 30% to about 50% of the *Cardiospermum halicacabum* extract, and from about 2% to about 10% of the *Bambusa arundinacea* extract, by weight relative to the total weight of the herbal composition. For example, in some embodiments, the herbal composition comprises from about 29% to about 35% of the *Vitex negundo* extract, from about 34% to about 40% of the

*Cardiospermum halicacabum* extract, and from about 4% to about 6% of the *Bambusa arundinacea* extract, by weight relative to the total weight of the herbal composition.

In some embodiments of the first aspect, the herbal composition comprises the *Citrus sinensis* extract and the *Bambusa arundinacea* extract. For example, in some embodiments, the herbal composition comprises a *Vitex negundo* extract, a *Cardiospermum halicacabum* extract, a *Citrus sinensis* extract, and a *Bambusa arundinacea* extract. In some embodiments, the herbal composition consists essentially of the *Vitex negundo* extract, the *Cardiospermum halicacabum* extract, the *Citrus sinensis* extract, and the *Bambusa arundinacea* extract. In some embodiments, the herbal composition consists of the *Vitex negundo* extract, the *Cardiospermum halicacabum* extract, the *Citrus sinensis* extract, the *Bambusa arundinacea* extract, and, optionally, at least one pharmaceutically acceptable excipient.

For example, in some embodiments of the first aspect, the herbal composition comprises from about 20% to about 40% of the *Vitex negundo* extract, from about 30% to about 50% of the *Cardiospermum halicacabum* extract, from about 2% to about 10% of the *Citrus sinensis* extract, and from about 2% to about 10% of the *Bambusa arundinacea* extract, by weight relative to the total weight of the herbal composition. For example, in some embodiments, the herbal composition comprises from about 29% to about 35% of the *Vitex negundo* extract, from about 34% to about 40% of the *Cardiospermum halicacabum* extract, from about 3% to about 6% of the *Citrus sinensis* extract, and from about 4% to about 6% of the *Bambusa arundinacea* extract, by weight relative to the total weight of the herbal composition.

In some embodiments of the first aspect, the herbal composition further comprises a *Boswellia serrata* extract or a *Curcuma longa* extract. For example, in some embodiments, the herbal composition comprises a *Vitex negundo* extract, a *Cardiospermum halicacabum* extract, and a *Boswellia serrata* extract or a *Curcuma longa* extract. In some embodiments, the herbal composition comprises a *Vitex negundo* extract, a *Cardiospermum halicacabum* extract, a *Citrus sinensis* extract, and a *Boswellia serrata* extract or a *Curcuma longa* extract. In some embodiments, the herbal composition comprises a *Vitex negundo* extract, a *Cardiospermum halicacabum* extract, a *Bambusa arundinacea* extract, and a *Boswellia serrata* extract or a *Curcuma longa* extract. In some embodiments, the herbal composition comprises a *Vitex negundo* extract, a *Cardiospermum halicacabum* extract, a *Citrus sinensis* extract, a *Bambusa arundinacea* extract, and a *Boswellia serrata* extract or a *Curcuma longa* extract. In some embodiments, the herbal composition consists essentially of the *Vitex negundo* extract, the *Cardiospermum halicacabum* extract, the *Citrus sinensis* extract, the *Bambusa arundinacea* extract, and the *Boswellia serrata* extract or the *Curcuma longa* extract. In some embodiments, the herbal composition consists of the *Vitex negundo* extract, the *Cardiospermum halicacabum* extract, the *Citrus sinensis* extract, the *Bambusa arundinacea* extract, the *Boswellia serrata* extract or the *Curcuma longa* extract, and, optionally, at least one pharmaceutically acceptable excipient.

In some embodiments of the first aspect, the herbal composition further comprises a *Boswellia serrata* extract and a *Curcuma longa* extract. For example, in some embodiments, the herbal composition comprises a *Vitex negundo* extract, a *Cardiospermum halicacabum* extract, a *Boswellia serrata* extract, and a *Curcuma longa* extract. In some embodiments, the herbal composition comprises a *Vitex negundo* extract, a *Cardiospermum halicacabum* extract, a *Citrus sinensis* extract, a *Boswellia serrata* extract, and a *Curcuma longa* extract. In some embodiments, the herbal composition comprises a *Vitex negundo* extract, a *Cardiospermum halicacabum* extract, a *Bambusa arundinacea* extract, a *Boswellia serrata* extract, and a *Curcuma longa* extract. In some embodiments, the herbal composition comprises a *Vitex negundo* extract, a *Cardiospermum halicacabum* extract, a *Citrus sinensis* extract, a *Bambusa arundinacea* extract, a *Boswellia serrata* extract, and a *Curcuma longa* extract. In some embodiments, the herbal composition consists essentially of the *Vitex negundo* extract, the *Cardiospermum halicacabum* extract, the *Citrus sinensis* extract, the *Bambusa arundinacea* extract, the *Boswellia serrata* extract, and the *Curcuma longa* extract. In some embodiments, the herbal composition consists of the *Vitex negundo* extract, the *Cardiospermum halicacabum* extract, the *Citrus sinensis* extract, the *Bambusa arundinacea* extract, the *Boswellia serrata* extract, the *Curcuma longa* extract, and, optionally, at least one pharmaceutically acceptable excipient.

In some embodiments of the first aspect, the herbal composition comprises from about 2% to about 10% of the *Boswellia serrata* extract, by weight relative to the total weight of the herbal composition. For example, in some embodiments, the herbal composition comprises from about 2% to about 8% of the *Boswellia serrata* extract, such as from about 2% to about 6%, from about 4% to about 8%, or from about 4% to about 6% of the *Boswellia serrata* extract, by weight relative to the total weight of the herbal composition. In some embodiments, the herbal composition comprises about 5% of the *Boswellia serrata* extract, by weight relative to the total weight of the herbal composition.

In some embodiments of the first aspect, the herbal composition comprises from about 5% to about 25% of the *Curcuma longa* extract, by weight relative to the total weight of the herbal composition. For example, in some embodiments, the herbal composition comprises from about 10% to about 20% of the *Curcuma longa* extract, such as from about 12% to about 20%, from about 10% to about 18%, or from about 12% to about 18% of the *Curcuma longa* extract, by weight relative to the total weight of the herbal composition. In some embodiments, the herbal composition comprises about 15% of the *Curcuma longa* extract, by weight relative to the total weight of the herbal composition.

For example, in some embodiments of the first aspect, the herbal composition comprises from about 20% to about 40% of the *Vitex negundo* extract, from about 30% to about 50% of the *Cardiospermum halicacabum* extract, from about 2% to about 10% of the *Citrus sinensis* extract, from about 2% to about 10% of the *Bambusa arundinacea* extract, from about 2% to about 10% of the *Boswellia serrata* extract, and from about 10% to about 20% of the *Curcuma longa* extract, by weight relative to the total weight of the herbal composition. For example, in some embodiments, the herbal composition comprises from about 29% to about 35% of the *Vitex negundo* extract, from about 34% to about 40% of the *Cardiospermum halicacabum* extract, from about 3% to about 6% of the *Citrus sinensis* extract, from about 4% to about 6% of the *Bambusa arundinacea* extract, from about 4% to about 6% of the *Boswellia serrata* extract, and from about 12% to about 18% of the *Curcuma longa* extract, by weight relative to the total weight of the herbal composition.

In some embodiments of the first aspect, the herbal composition further comprises at least one additional herbal extract chosen from a Green tea extract, a *Delonix elata* extract, an *Aesculus hippocastanum* extract, a *Citrus limon* extract, an Ashwagandha extract, a *Murraya koenigii* extract, a *Bacopa monnieri* extract, an *Evolvulus alsinoides* extract, a *Wrightia tinctoria* extract, a *Sophora japonica* extract, a *Cissus quadrangularis* extract, a *Commiphora mukul* extract, a *Terminalia arjuna* extract, a *Momordica charantia* extract, a *Phyllanthus niruri* extract, an *Ocimum sanctum* extract, and combinations thereof.

In some embodiments of the first aspect, the herbal composition does not comprise glucosamine. Thus, in some embodiments, the herbal compositions of the first aspect may improve joint health and reduce or alleviate at least one symptom of osteoarthritis while avoiding the side effects commonly encountered with high-dose glucosamine supplementation, and thus may be taken for extended periods, or indefinitely.

In some embodiments of the first aspect, the herbal composition does not comprise a natural oil such as flax seed oil, sesame seed oil, castor oil, sunflower oil, soybean oil, safflower oil, corn oil, hemp oil, palm oil, or peanut oil.

In a second aspect, the present disclosure is directed to an herbal composition comprising a *Vitex negundo* extract, a *Cardiospermum halicacabum* extract, and glucosamine. In some embodiments, the herbal composition comprises from about 5% to about 40% of the *Vitex negundo* extract, from about 10% to about 50% of the *Cardiospermum halicacabum* extract, and from about 30% to about 50% of the glucosamine, by weight relative to the total weight of the herbal composition. In some embodiments, the herbal composition consists essentially of the *Vitex negundo* extract, the *Cardiospermum halicacabum* extract, and the glucosamine. In some embodiments, the herbal composition consists of the *Vitex negundo* extract, the *Cardiospermum halicacabum* extract, the glucosamine, and, optionally, at least one pharmaceutically acceptable excipient.

In some embodiments of the second aspect, the herbal composition comprises from about 30% to about 50% glucosamine, such as from about 30% to about 45%, from about 35% to about 50%, from about 35% to about 45%, from about 35% to about 42%, or from about 37% to about 42% glucosamine, by weight relative to the total weight of the herbal composition. In some embodiments, the herbal composition comprises about 40% glucosamine, by weight relative to the total weight of the herbal composition. In some embodiments, the glucosamine is present in at least one form chosen from glucosamine sulfate, glucosamine hydrochloride, n-acetyl glucosamine, glucosamine sulfate potassium chloride, glucosamine sulfate sodium chloride, vegetarian glucosamine, and combinations thereof. In some embodiments, the glucosamine is present in the form of glucosamine sulfate.

In some embodiments of the second aspect, the herbal composition comprises from about 5% to about 20% of the *Vitex negundo* extract, such as from about 5% to about 15%, from about 5% to about 12%, from about 8% to about 20%, from about 8% to about 15%, or from about 8% to about 12% of the *Vitex negundo* extract, by weight relative to the total weight of the herbal composition. In some embodiments, the herbal composition comprises about 10% of the *Vitex negundo* extract, by weight relative to the total weight of the herbal composition.

In some embodiments of the second aspect, the herbal composition comprises from about 10% to about 30% of the *Cardiospermum halicacabum* extract, such as from about 15% to about 30%, from about 15% to about 25%, from about 15% to about 22%, from about 18% to about 30%, from about 18% to about 25%, or from about 18% to about 22% of the *Cardiospermum halicacabum* extract, by weight relative to the total weight of the herbal composition. In some embodiments, the herbal composition comprises about 20% of the *Cardiospermum halicacabum* extract, by weight relative to the total weight of the herbal composition.

For example, in some embodiments of the second aspect, the herbal composition comprises from about 5% to about 20% of the *Vitex negundo* extract, from about 10% to about 30% of the *Cardiospermum halicacabum* extract, and from about 30% to about 50% of the glucosamine, by weight relative to the total weight of the herbal composition. For example, in some embodiments, the herbal composition comprises from about 8% to about 15% of the *Vitex negundo* extract, from about 18% to about 25% of the *Cardiospermum halicacabum* extract, and from about 35% to about 45% of the glucosamine, by weight relative to the total weight of the composition.

In some embodiments of the second aspect, the weight ratio of the *Vitex negundo* extract to the *Cardiospermum halicacabum* extract ranges from about 1.2:1 to about 1:3, such as from about 1.2:1 to about 1:2.5, from about 1:1 to about 1:3, or from about 1:1 to about 1:2.5. For example, in some embodiments of the second aspect, the weight ratio of the *Vitex negundo* extract to the *Cardiospermum halicacabum* extract ranges from about 1:1.5 to about 1:3, from about 1:1.5 to about 1:2.5, from about 1:1.5 to about 1:2.2, from about 1:1.7 to about 1:3, from about 1:1.7 to about 1:2.5, from about 1:1.7 to about 1:2.2, from about 1:2 to about 1:3, from about 1:2 to about 1:2.5, or from about 1:2 to about 1:2.2. In other embodiments of the second aspect, the weight ratio of the *Vitex negundo* extract to the *Cardiospermum halicacabum* extract ranges from about 1.2:1 to about 1:2, from about 1.2:1 to about 1:1.5, from about 1.2:1 to about 1:1.2, from about 1:1 to about 1:2, from about 1:1 to about 1:1.5, from about 1:1 to about 1:1.2, from about 1:1.1 to about 1:2, from about 1:1.1 to about 1:1.5, or from about 1:1.1 to about 1:1.2.

In some embodiments of the second aspect, the herbal composition further comprises a *Citrus sinensis* extract. For example, in some embodiments, the herbal composition comprises a *Vitex negundo* extract, a *Cardiospermum halicacabum* extract, a *Citrus sinensis* extract, and glucosamine. In some embodiments, the herbal composition consists essentially of the *Vitex negundo* extract, the *Cardiospermum halicacabum* extract, the *Citrus sinensis* extract, and the glucosamine. In some embodiments, the herbal composition consists of the *Vitex negundo* extract, the *Cardiospermum halicacabum* extract, the *Citrus sinensis* extract, the glucosamine, and, optionally, at least one pharmaceutically acceptable excipient.

In some embodiments of the second aspect, the herbal composition comprises from about 2% to about 10% of the *Citrus sinensis* extract, by weight relative to the total weight of the herbal composition, such as from about 2% to about 8%, from about 2% to about 6%, from about 3% to about 8%, or from about 3% to about 6% of the *Citrus sinensis* extract, by weight relative to the total weight of the herbal composition. In some embodiments, the herbal composition comprises about 4% of the *Citrus sinensis* extract, by weight relative to the total weight of the herbal composition.

For example, in some embodiments of the second aspect, the herbal composition comprises from about 5% to about 20% of the *Vitex negundo* extract, from about 10% to about 30% of the *Cardiospermum halicacabum* extract, from about 2% to about 10% of the *Citrus sinensis* extract, and from about 30% to about 50% of the glucosamine, by weight relative to the total weight of the herbal composition. For example, in some embodiments, the herbal composition comprises from about 8% to about 15% of the *Vitex negundo* extract, from about 18% to about 25% of the *Cardiospermum halicacabum* extract, from about 3% to about 6% of the *Citrus sinensis* extract, and from about 35% to about 45% of the glucosamine, by weight relative to the total weight of the herbal composition.

In some embodiments of the second aspect, the herbal composition further comprises a *Bambusa arundinacea* extract. For example, in some embodiments, the herbal composition comprises a *Vitex negundo* extract, a *Cardiospermum halicacabum* extract, a *Bambusa arundinacea* extract, and glucosamine. In some embodiments, the herbal composition consists essentially of the *Vitex negundo* extract, the *Cardiospermum halicacabum* extract, the *Bambusa arundinacea* extract, and the glucosamine. In some embodiments, the herbal composition consists of the *Vitex negundo* extract, the *Cardiospermum halicacabum* extract, the *Bambusa arundinacea* extract, the glucosamine, and, optionally, at least one pharmaceutically acceptable excipient.

In some embodiments of the second aspect, the herbal composition comprises from about 2% to about 10% of the *Bambusa arundinacea* extract, by weight relative to the total weight of the herbal composition, such as from about 2% to about 8%, from about 2% to about 6%, from about 4% to about 8%, or from about 4% to about 6% of the *Bambusa arundinacea* extract, by weight relative to the total weight of the herbal composition. In some embodiments, the herbal composition comprises about 5% of the *Bambusa arundinacea* extract, by weight relative to the total weight of the herbal composition.

For example, in some embodiments of the second aspect, the herbal composition comprises from about 5% to about 20% of the *Vitex negundo* extract, from about 10% to about 30% of the *Cardiospermum halicacabum* extract, from about 2% to about 10% of the *Bambusa arundinacea* extract, and from about 30% to about 50% of the glucosamine, by weight relative to the total weight of the herbal composition. For example, in some embodiments, the herbal composition comprises from about 8% to about 15% of the *Vitex negundo* extract, from about 18% to about 25% of the *Cardiospermum halicacabum* extract, from about 4% to about 6% of the *Bambusa arundinacea* extract, and from about 35% to about 45% of the glucosamine, by weight relative to the total weight of the herbal composition.

In some embodiments of the second aspect, the herbal composition comprises the *Citrus sinensis* extract and the *Bambusa arundinacea* extract. For example, in some embodiments, the herbal composition comprises a *Vitex negundo* extract, a *Cardiospermum halicacabum* extract, a *Citrus sinensis* extract, a *Bambusa arundinacea* extract, and glucosamine. In some embodiments, the herbal composition consists essentially of the *Vitex negundo* extract, the *Cardiospermum halicacabum* extract, the *Citrus sinensis* extract, the *Bambusa arundinacea* extract, and the glucosamine. In some embodiments, the herbal composition consists of the *Vitex negundo* extract, the *Cardiospermum halicacabum* extract, the *Citrus sinensis* extract, the *Bambusa arundinacea* extract, the glucosamine, and, optionally, at least one pharmaceutically acceptable excipient.

For example, in some embodiments of the second aspect, the herbal composition comprises from about 5% to about 20% of the *Vitex negundo* extract, from about 10% to about 30% of the *Cardiospermum halicacabum* extract, from about 2% to about 10% of the *Citrus sinensis* extract, from about 2% to about 10% of the *Bambusa arundinacea* extract, and from about 30% to about 50% of the glucosamine, by weight relative to the total weight of the herbal composition.

For example, in some embodiments, the herbal composition comprises from about 8% to about 15% of the *Vitex negundo* extract, from about 18% to about 25% of the *Cardiospermum halicacabum* extract, from about 3% to about 6% of the *Citrus sinensis* extract, from about 4% to about 6% of the *Bambusa arundinacea* extract, and from about 35% to about 45% of the glucosamine, by weight relative to the total weight of the herbal composition.

In some embodiments of the second aspect, the herbal composition further comprises a *Boswellia serrata* extract or a *Curcuma longa* extract. For example, in some embodiments, the herbal composition comprises a *Vitex negundo* extract, a *Cardiospermum halicacabum* extract, glucosamine, and a *Boswellia serrata* extract or a *Curcuma longa* extract. In some embodiments, the herbal composition comprises a *Vitex negundo* extract, a *Cardiospermum halicacabum* extract, a *Citrus sinensis* extract, glucosamine, and a *Boswellia serrata* extract or a *Curcuma longa* extract. In some embodiments, the herbal composition comprises a *Vitex negundo* extract, a *Cardiospermum halicacabum* extract, a *Bambusa arundinacea* extract, glucosamine, and a *Boswellia serrata* extract or a *Curcuma longa* extract. In some embodiments, the herbal composition comprises a *Vitex negundo* extract, a *Cardiospermum halicacabum* extract, a *Citrus sinensis* extract, a *Bambusa arundinacea* extract, glucosamine, and a *Boswellia serrata* extract or a *Curcuma longa* extract. In some embodiments, the herbal composition consists essentially of the *Vitex negundo* extract, the *Cardiospermum halicacabum* extract, the *Citrus sinensis* extract, the *Bambusa arundinacea* extract, the glucosamine, and the *Boswellia serrata* extract or the *Curcuma longa* extract. In some embodiments, the herbal composition consists of the *Vitex negundo* extract, the *Cardiospermum halicacabum* extract, the *Citrus sinensis* extract, the *Bambusa arundinacea* extract, the glucosamine, the *Boswellia serrata* extract or the *Curcuma longa* extract, and, optionally, at least one pharmaceutically acceptable excipient.

In some embodiments of the second aspect, the herbal composition further comprises a *Boswellia serrata* extract and a *Curcuma longa* extract. For example, in some embodiments, the herbal composition comprises a *Vitex negundo* extract, a *Cardiospermum halicacabum* extract, a *Boswellia serrata* extract, a *Curcuma longa* extract, and glucosamine. In some embodiments, the herbal composition comprises a *Vitex negundo* extract, a *Cardiospermum halicacabum* extract, a *Citrus sinensis* extract, a *Boswellia serrata* extract, a *Curcuma longa* extract, and glucosamine. In some embodiments, the herbal composition comprises a *Vitex negundo* extract, a *Cardiospermum halicacabum* extract, a *Bambusa arundinacea* extract, a *Boswellia serrata* extract, a *Curcuma longa* extract, and glucosamine. In some embodiments, the herbal composition comprises a *Vitex negundo* extract, a *Cardiospermum halicacabum* extract, a *Citrus sinensis* extract, a *Bambusa arundinacea* extract, a *Boswellia serrata* extract, a *Curcuma longa* extract, and glucosamine. In some embodiments, the herbal composition consists essentially of the *Vitex negundo* extract, the *Cardiospermum halicacabum* extract, the *Citrus sinensis* extract, the *Bambusa arundinacea* extract, the *Boswellia serrata* extract, the *Curcuma longa* extract, and the glucosamine. In some embodiments, the herbal composition consists of the *Vitex negundo* extract, the *Cardiospermum halicacabum* extract, the *Citrus sinensis* extract, the *Bambusa arundinacea* extract, the *Boswellia serrata* extract, the *Curcuma longa* extract, the glucosamine, and, optionally, at least one pharmaceutically acceptable excipient.

In some embodiments of the second aspect, the herbal composition comprises from about 2% to about 10% of the *Boswellia serrata* extract, by weight relative to the total weight of the herbal composition. For example, in some embodiments, the herbal composition comprises from about 2% to about 8% of the *Boswellia serrata* extract, such as from about 2% to about 6%, from about 4% to about 8%, or from about 4% to about 6% of the *Boswellia serrata* extract, by weight relative to the total weight of the herbal composition. In some embodiments, the herbal composition comprises about 5% of the *Boswellia serrata* extract, by weight relative to the total weight of the herbal composition.

In some embodiments of the second aspect, the herbal composition comprises from about 5% to about 25% of the *Curcuma longa* extract, by weight relative to the total weight of the herbal composition. For example, in some embodiments, the herbal composition comprises from about 10% to about 20% of the *Curcuma longa* extract, such as from about 12% to about 20%, from about 10% to about 18%, or from about 12% to about 18% of the *Curcuma longa* extract, by weight relative to the total weight of the herbal composition. In some embodiments, the herbal composition comprises about 15% of the *Curcuma longa* extract, by weight relative to the total weight of the herbal composition.

For example, in some embodiments of the second aspect, the herbal composition comprises from about 5% to about 20% of the *Vitex negundo* extract, from about 10% to about 30% of the *Cardiospermum halicacabum* extract, from about 2% to about 10% of the *Citrus sinensis* extract, from about 2% to about 10% of the *Bambusa arundinacea* extract, from about 2% to about 10% of the *Boswellia serrata* extract, from about 10% to about 20% of the *Curcuma longa* extract, and from about 30% to about 50% of the glucosamine, by weight relative to the total weight of the herbal composition. For example, in some embodiments, the herbal composition comprises from about 8% to about 15% of the *Vitex negundo* extract, from about 18% to about 25% of the *Cardiospermum halicacabum* extract, from about 3% to about 6% of the *Citrus sinensis* extract, from about 4% to about 6% of the *Bambusa arundinacea* extract, from about 4% to about 6% of the *Boswellia serrata* extract, from about 12% to about 18% of the *Curcuma longa* extract, and from about 35% to about 45% of the glucosamine, by weight relative to the total weight of the composition.

In some embodiments of the second aspect, the herbal composition further comprises at least one additional herbal extract chosen from a Green tea extract, a *Delonix elata* extract, an *Aesculus hippocastanum* extract, a *Citrus limon* extract, an Ashwagandha extract, a *Murraya koenigii* extract, a *Bacopa monnieri* extract, an *Evolvulus alsinoides* extract, a *Wrightia tinctoria* extract, a *Sophora japonica* extract, a *Cissus quadrangularis* extract, a *Commiphora mukul* extract, a *Terminalia arjuna* extract, a *Momordica charantia* extract, a *Phyllanthus niruri* extract, an *Ocimum sanctum* extract, and combinations thereof.

By providing a relatively low dose of glucosamine (e.g., about 400 mg/day) in combination with the potent herbal extracts of the present disclosure, herbal compositions according to the second aspect may improve joint health and reduce or alleviate at least one symptom of osteoarthritis while avoiding the side effects commonly associated with high-dose glucosamine supplementation, and thus may be taken for extended periods, or indefinitely.

In some embodiments of the second aspect, the herbal composition does not comprise a natural oil such as flax seed oil, sesame seed oil, castor oil, sunflower oil, soybean oil, safflower oil, corn oil, hemp oil, palm oil, or peanut oil.

In some embodiments, the herbal compositions of the present disclosure may comprise at least one pharmaceutically acceptable excipient, for example, to thicken, dilute, emulsify, stabilize, preserve, protect, color, flavor, and/or fashion the herbal extracts into an applicable and efficacious preparation, such that it may be safe, convenient, and/or otherwise acceptable for use. In some embodiments, the herbal composition may comprise from about 0 to about 10% of at least one pharmaceutically acceptable excipient, such as from about 0.5% to about 5% of at least one pharmaceutically acceptable excipient, by weight relative to the total weight of the herbal composition. In some embodiments, the herbal composition comprises less than 5%, such as less than 4%, less than 3%, less than 2%, or less than 1% of pharmaceutically acceptable excipients and residual extraction solvent, by weight relative to the total weight of the herbal composition.

In some embodiments, the herbal compositions of the present disclosure may further comprise at least one antioxidant. Examples of antioxidants suitable for the present disclosure include, but are not limited to, alpha-tocopherol (vitamin E), calcium disodium EDTA, alpha tocoferylacetates, butylhydroxytoluenes (BHT), butylhydroxyanisoles (BHA), green tea extract, grape seed extract, *Ginkgo biloba* extract, blueberry extract, rosemary extract, and any combinations thereof.

The herbal compositions of the present disclosure may be administered to a subject via different routes, such as orally or topically. Thus, in a third aspect, the present disclosure is directed to a dosage form for oral or topical administration comprising an herbal composition according to the present disclosure. In some embodiments, the herbal compositions of the present disclosure may be provided in any form suitable for oral or topical administration, such as, for example, in the form of a pill, capsule, tablet, sachet, oral solution, oral suspension, lotion, cream, salve, spray, or patch. The dosage forms can be prepared according to processes known in the art and may include one or more pharmaceutically-acceptable excipients as discussed above.

In some embodiments, the dosage form is a dosage form for oral administration comprising an herbal composition of the present disclosure. The herbal composition may be any herbal composition of the present disclosure, such as, for example, any of the herbal compositions discussed above with reference to the first aspect or the second aspect of the present disclosure. In some embodiments, the dosage form may be a pill, a tablet, a capsule, an oral solution, an oral suspension, an oral spray, or any other dosage form suitable for oral administration. The dosage form may be solid or liquid. When solid, the dosage form may be of any size and shape suitable for oral administration. In some embodiments, the dosage form is a capsule. In some embodiments, the capsule is a gelatin capsule, a polysaccharide capsule, or a vegetarian capsule. The capsule may be a hard capsule or a soft capsule. In some embodiments, the dosage form for oral administration further comprises at least one pharmaceutically acceptable excipient, as discussed above.

In some embodiments, the dosage form for oral administration comprises from about 0.1 g to about 1.0 g of an herbal composition of the present disclosure, such as, for example, from about 0.1 g to about 0.8 g, from about 0.1 g to about 0.6 g, from about 0.4 g to about 1.0 g, from about 0.4 g to about 0.8 g, or from about 0.4 g to about 0.6 g of an herbal composition of the present disclosure. For example, in some embodiments, the dosage form for oral administration may comprise about 0.1, 0.2, 0.3, 0.4, 0.5, 0.6, 0.7, 0.8, 0.9, or 1.0 g of an herbal composition of the present disclosure. In some embodiments, the dosage form for oral administration comprises about 0.5 g of an herbal composition of the present disclosure. In some embodiments, the dosage form for oral administration comprises about 1.0 g of an herbal composition of the present disclosure.

For example, in some embodiments of the third aspect, there is provided a dosage form for oral administration comprising an herbal composition comprising a *Vitex negundo* extract, a *Cardiospermum halicacabum* extract, a *Citrus sinensis* extract, a *Bambusa arundinacea* extract, a *Boswellia serrata* extract, and a *Curcuma longa* extract. In some embodiments, the dosage form is a capsule. In some embodiments, the dosage form comprises about 0.5 g of the herbal composition. In some embodiments, the dosage form further comprises at least one pharmaceutically acceptable excipient. In some embodiments, the herbal composition comprises from about 20% to about 40% of the *Vitex negundo* extract, from about 30% to about 50% of the *Cardiospermum halicacabum* extract, from about 2% to about 10% of the *Citrus sinensis* extract, from about 2% to about 10% of the *Bambusa arundinacea* extract, from about 2% to about 10% of the *Boswellia serrata* extract, and from about 10% to about 20% of the *Curcuma longa* extract, by weight relative to the total weight of the herbal composition. For example, in one embodiment, the dosage form is a capsule comprising about 162.5 mg of a *Vitex negundo* extract, about 187.5 mg of a *Cardiospermum halicacabum* extract, about 25 mg of a *Citrus sinensis* extract, about 25 mg of a *Bambusa arundinacea* extract, about 25 mg of a *Boswellia serrata* extract, about 75 mg of a *Curcuma longa* extract, and, optionally, at least one pharmaceutically acceptable excipient. In some embodiments, the dosage form does not comprise glucosamine.

In another embodiment of the third aspect, there is provided a dosage form for oral administration comprising an herbal composition comprising a *Vitex negundo* extract, a *Cardiospermum halicacabum* extract, a *Citrus sinensis* extract, a *Boswellia serrata* extract, a *Curcuma longa* extract, and glucosamine. In some embodiments, the dosage form is a capsule. In some embodiments, the dosage form comprises about 0.5 g of the herbal extract. In some embodiments, the dosage form further comprises at least one pharmaceutically acceptable excipient. In some embodiments, the herbal composition comprises from about 5% to about 20% of the *Vitex negundo* extract, from about 10% to about 30% of the *Cardiospermum halicacabum* extract, from about 2% to about 10% of the *Citrus sinensis* extract, from about 2% to about 10% of the *Bambusa arundinacea* extract, from about 2% to about 10% of the *Boswellia serrata* extract, from about 10% to about 20% of the *Curcuma longa* extract, and from about 30% to about 50% of the glucosamine, by weight relative to the total weight of the herbal composition. For example, in one embodiment, the dosage form is a capsule comprising about 50 mg of a *Vitex negundo* extract, about 104 mg of a *Cardiospermum halicacabum* extract, about 21 mg of a *Citrus sinensis* extract, about 25 mg of a *Bambusa arundinacea* extract, about 25 mg of a *Boswellia serrata* extract, about 75 mg of a *Curcuma longa* extract, about 200 mg of glucosamine sulfate, and, optionally, at least one pharmaceutically acceptable excipient.

In some embodiments of the third aspect, the dosage form is a dosage form for topical administration comprising an herbal composition of the present disclosure. The herbal composition may be any herbal composition of the present disclosure, such as, for example, any of the herbal compositions discussed above with reference to the first aspect or the second aspect of the present disclosure. In some embodiments, the dosage form may be a solution, suspension, lotion, cream, salve, spray, patch, or any other dosage form suitable for topical administration. In some embodiments, the dosage form for topical administration may comprise at least one pharmaceutically acceptable excipient, as discussed above. In some embodiments, the dosage form for topical administration may comprise an herbal composition according to the present disclosure and *Aloe vera*.

In some embodiments, the dosage form for topical administration comprises from about 0.1 g to about 100 g of an herbal composition of the present disclosure, such as, for example, from about 50 g to about 100 g, from about 0.5 g to about 50 g, from about 10 g to about 80 g, from about 20 g to about 70 g, from about 30 g to about 60 g. For example, in some embodiments, the dosage form for topical administration may comprise about 10, 20, 30, 40, 50, 60, 70, 80, 90, or 100 g of an herbal composition of the present invention. In some embodiments, the dosage form for topical administration comprises from about 0.1 g to about 10 g of an herbal composition of the present disclosure, such as, for example, from about 0.5 g to about 10 g, from about 0.5 g to about 8 g, from about 0.5 g to about 6 g, from about 0.5 g to about 5 g, from about 0.5 g to about 4 g, from about 2 g to about 10 g, from about 2 g to about 8 g, from about 2 g to about 6 g, from about 2 g to about 5 g, or from about 2 g to about 4 g of an herbal composition of the present disclosure. For example, in some embodiments, the dosage form for topical administration may comprise about 1, 2, 3, 4, 5, 6, 7, 8, 9, or 10 g of an herbal composition of the present disclosure.

The present disclosure further encompasses methods of improving joint health by administering an herbal composition of the present disclosure to a subject in need thereof. Thus, in a fourth aspect, the present disclosure is directed to a method of improving joint health in a subject, comprising administering to the subject an herbal composition of the present disclosure. The herbal composition may be any herbal composition of the present disclosure, such as, for example, any of the herbal compositions discussed above within the context of the first and second aspects of the present disclosure.

In some embodiments of the fourth aspect, the subject is a mammal. In some embodiments, the subject is a human. In some embodiments, the subject has osteoarthritis. In some embodiments, the osteoarthritis is mild to moderate osteoarthritis. In some embodiments, the osteoarthritis is knee osteoarthritis, hand osteoarthritis, hip osteoarthritis, spine osteoarthritis, or any combination thereof. In some embodiments, the osteoarthritis is knee osteoarthritis. In some embodiments, the osteoarthritis may be clinically diagnosed. In some embodiments, the osteoarthritis may be diagnosed with radiological evidence, such as x-rays.

In some embodiments of the fourth aspect, the herbal composition of the present disclosure is administered orally. In some embodiments, the oral daily dosage of the herbal composition ranges from about 0.1 g to about 4 g, such as from about 0.5 g to about 4 g, from about 0.5 g to about 3 g, from about 0.5 g to about 2 g, from about 0.5 g to about 1.5 g, from about 0.5 g to about 1.2 g, from about 0.8 g to about 4 g, from about 0.8 g to about 3 g, from about 0.8 g to about 2 g, from about 0.8 g to about 1.5 g, or from about 0.8 g to about 1.2 g per day. For example, in some embodiments, the daily dosage of the herbal composition is about 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, or 4.0 g per day orally. In some embodiments, the daily dosage is about 1 g per day orally.

In some embodiments of the fourth aspect, the herbal composition is administered orally one, two, three, or more than three times per day. In some embodiments, the herbal composition is administered twice per day orally. For example, in some embodiments, about 0.5 g of the herbal composition is administered orally twice per day, for a total daily dosage of about 1 g per day. In other embodiments, about 1 g of the herbal composition is administered orally once per day, for a total daily dose of about 1 g per day. In some embodiments, the herbal composition is administered orally for at least 30 days, such as for at least 60 days, at least 90 days, at least 120 days, or longer.

As discussed above with respect to the third aspect, the herbal compositions of the present disclosure may be administered orally in any form suitable for oral administration. For example, in some embodiments, the herbal composition may be administered to the subject in the form of a pill, a tablet, a capsule, an oral solution, an oral suspension, or in any other form suitable for oral administration. In some embodiments, the herbal composition is administered in capsule form. For example, in some embodiments, a capsule comprising about 0.5 g of the herbal composition may be administered twice per day to provide a total daily dosage of about 1 g of the herbal composition. In another embodiment, a capsule comprising about 1 g of the herbal composition may be administered once per day, for a total daily dosage of about 1 g of the herbal composition.

For example, in some embodiments of the fourth aspect, there is provided a method of improving joint health in a subject, comprising administering to the subject an herbal composition comprising a *Vitex negundo* extract, a *Cardiospermum halicacabum* extract, a *Citrus sinensis* extract, a *Bambusa arundinacea* extract, a *Boswellia serrata* extract, and a *Curcuma longa* extract. For example, in some embodiments, the method comprises administering to the subject about 1 g/day of an herbal composition comprising from about 20% to about 40% of a *Vitex negundo* extract, from about 30% to about 50% of a *Cardiospermum halicacabum* extract, from about 2% to about 10% of a *Citrus sinensis* extract, from about 2% to about 10% of a *Bambusa arundinacea* extract, from about 2% to about 10% of a *Boswellia serrata* extract, and from about 10% to about 20% of a *Curcuma longa* extract, by weight relative to the total weight of the herbal composition. For example, in one embodiment, the method comprises administering to the subject about 325 mg/day of a *Vitex negundo* extract, about 375 mg/day of a *Cardiospermum halicacabum* extract, about 50 mg/day of a *Citrus sinensis* extract, about 50 mg/day of a *Bambusa arundinacea* extract, about 50 mg/day of a *Boswellia serrata* extract, and about 150 mg/day of a *Curcuma longa* extract.

In another embodiment of the fourth aspect, there is provided a method of improving joint health in a subject, comprising administering to the subject an herbal composition comprising a *Vitex negundo* extract, a *Cardiospermum halicacabum* extract, a *Citrus sinensis* extract, a *Bambusa arundinacea* extract, a *Boswellia serrata* extract, a *Curcuma longa* extract, and glucosamine. For example, in some embodiments, the method comprises administering to the subject about 1 g/day of an herbal composition comprising from about 5% to about 20% of a *Vitex negundo* extract, from about 10% to about 30% of a *Cardiospermum halicacabum* extract, from about 2% to about 10% of a *Citrus sinensis* extract, from about 2% to about 10% of a *Bambusa arundinacea* extract, from about 2% to about 10% of a *Boswellia serrata* extract, from about 10% to about 20% of a *Curcuma longa* extract, and from about 30% to about 50% of glucosamine, by weight relative to the total weight of the herbal composition. For example, in one embodiment, the method comprises administering to the subject about 100 mg/day of a *Vitex negundo* extract, about 208 mg/day of a *Cardiospermum halicacabum* extract, about 42 mg/day of a *Citrus sinensis* extract, about 50 mg/day of a *Bambusa arundinacea* extract, about 50 mg/day of a *Boswellia serrata* extract, about 150 mg/day of a *Curcuma longa* extract, and about 400 mg/day of glucosamine sulfate.

In some embodiments of the fourth aspect, the herbal composition of the present disclosure is administered topically. In some embodiments, the topical daily dosage of the herbal composition ranges from about 0.1 g to about 100 g, such as, for example, from about 50 g to about 100 g, from about 0.5 g to about 50 mg, from about 10 g to about 80 g, from about 20 g to about 70 g, from about 30 g to about 60 g. For example, in some embodiments, the dosage form for topical administration may comprise about 10, 20, 30, 40, 50, 60, 70, 80, 90, or 100 g of an herbal composition of the present invention. In some embodiments, the dosage form for topical administration comprises from about 0.1 g to about 10 g of an herbal composition of the present disclosure, such as from about 0.5 g to about 10 g, from about 0.5 g to about 8 g, from about 0.5 g to about 6 g, from about 0.5 g to about 5 g, from about 0.5 g to about 4 g, from about 2 g to about 10 g, from about 2 g to about 8 g, from about 2 g to about 6 g, from about 2 g to about 5 g, or from about 2 g to about 4 g. For example, in some embodiments, the daily dosage of the herbal composition is about 1, 2, 3, 4, 5, 6, 7, 8, 9, or 10 g per day topically. In some embodiments, the herbal composition may be administered topically one, two, three, or more than three times per day. In some embodiments, the herbal composition may be administered topically for at least 30 days, such as for at least 60 days, at least 90 days, at least 120 days, or longer.

As discussed above with respect to the third aspect, the herbal compositions of the present disclosure may be administered topically in any form suitable for topical administration. For example, in some embodiments, the herbal composition may be administered to the subject in the form of a solution, suspension, lotion, cream, salve, spray, patch, or any other dosage form suitable for topical administration. In some embodiments, the dosage form for topical administration may comprise an herbal composition according to the present disclosure and *Aloe vera*.

In some embodiments of the fourth aspect, improving joint health comprises alleviating or reducing the severity of at least one symptom of osteoarthritis, such as, for example, pain, stiffness, tenderness, reduced flexibility, grating sensation, bone spurs, swelling, or any combination thereof. Thus, in some embodiments, there is provided a method of reducing the severity of at least one symptom of osteoarthritis in a subject with osteoarthritis, comprising administering to the subject an herbal composition of the present disclosure.

In some embodiments of the fourth aspect, the improvement in joint health may be measured by changes in baseline versus end point scores in the 30 second chair stand test (30SCST). Thus, in some embodiments, there is provided a method of improving the 30 second chair stand test (30SCST) score in a subject with osteoarthritis comprising administering to the subject an herbal composition of the present disclosure for at least 30 days, at least 60 days, at least 90 days, at least 120 days, or longer. In some embodiments, the improvement in the 30SCST at 120 days is at least 8%, at least 10%, at least 13%, at least 15%, at least 16%, or at least about 18%.

In some embodiments of the fourth aspect, the improvement in joint health may be measured by changes in baseline versus end point in the Western Ontario and McMaster Universities Osteoarthritis Index (WOMAC) scores on the pain subscale (WOMAC A), the stiffness subscale (WOMAC B), and/or the physical function subscale (WOMAC C). Thus, in some embodiments, there is provided a method of reducing the WOMAC A, WOMAC B, and/or WOMAC C score in a subject with osteoarthritis comprising administering to the subject an herbal composition of the present disclosure for at least 30 days, at least 60 days, at least 90 days, at least 120 days, or longer. In some embodiments, the reduction in WOMAC A (pain) score at 120 days is at least 50%, at least 55%, at least 60%, at least 65%, or at least 70%. In some embodiments, the reduction in WOMAC B (stiffness) score at 120 days is at least 50%, at least 55%, at least 60%, at least 65%, or at least 70%. In some embodiments, the reduction in WOMAC C (physical function) score at 120 days is at least 55%, at least 60%, at least 65%, or at least 70%.

In some embodiments of the fourth aspect, the improvement in joint health may be measured by changes in baseline versus end point range of motion in knee flexion. Thus, in some embodiments, there is provided a method of improving the range of motion in knee flexion in a subject with osteoarthritis comprising administering to the subject an herbal composition of the present disclosure for at least 30 days, at least 60 days, at least 90 days, at least 120 days, or longer. In some embodiments, the range of motion in knee flexion at 120 days is improved by at least 4%, at least 5%, at least 6%, or at least 7%.

In some embodiments of the fourth aspect, the improvement in joint health may be measured by changes in baseline versus end point radiographic minimum joint space width. Thus, in some embodiments, there is provided a method of improving the radiographic minimum joint space width in a subject with osteoarthritis comprising administering to the subject an herbal composition of the present disclosure for at least 30 days, at least 60 days, at least 90 days, at least 120 days, or longer. In some embodiments, the radiographic minimum joint space width at 120 days is improved by at least 15%, at least 20%, at least 23%, or at least 24%.

In a fifth aspect, the present disclosure is directed to a method of making an herbal composition comprising: extracting *Vitex negundo* aerial parts to form a *Vitex negundo* extract; extracting *Cardiospermum halicacabum* aerial parts to form a *Cardiospermum halicacabum* extract; combining the *Vitex negundo* extract and the *Cardiospermum halicacabum* extract; and blending the combined extracts.

In some embodiments, the method further comprises: extracting *Citrus sinensis* peels to form a *Citrus sinensis* extract, extracting *Bambusa arundinacea* shoots to form a *Bambusa arundinacea* extract, extracting *Boswellia serrata* gum resin to form a *Boswellia serrata* extract, and extracting *Curcuma longa* rhizomes to form a *Curcuma longa* extract; combining the *Citrus sinensis* extract, the *Bambusa arundinacea* extract, the *Boswellia serrata* extract, and the *Curcuma longa* extract with the *Vitex negundo* extract and the *Cardiospermum halicacabum* extract; and blending the combined extracts.

In some embodiments, the herbal parts are dried and powdered before extraction. In some embodiments, the herbal parts are extracted with an extraction solvent chosen from water, alcohol, and combinations thereof. In some embodiments, the extraction solvent is water. In some embodiments, the water is acidified with at least one acid. In some embodiments, the extraction solvent comprises at least one aqueous alcohol, such as aqueous methanol, aqueous ethanol, or combinations thereof. In some embodiments, the aqueous alcohol is acidified with at least one acid. In some embodiments, the aqueous alcohol comprises at least about 1% alcohol by volume, such as at least about 5%, 10%, 15%, 20%, 30%, 40%, 50%, 60%, 70%, 80%, 90%, or at least about 95% alcohol by volume. In some embodiments, the aqueous alcohol comprises at least about 5% water by volume, such as at least about 10%, 15%, 20%, 30%, 40%, 50%, 60%, 70%, 80%, 90%, 95%, or at least about 99% water by volume. In some embodiments, the aqueous alcohol comprises about 5% to about 99% water and about 95% to about 1% alcohol by volume. In some embodiments, the aqueous alcohol comprises about 50% to about 95% water and about 50% to about 5% alcohol by volume, such as about 50% to about 95% water and about 50% to about 5% ethanol by volume. In some embodiments, the aqueous alcohol comprises about 95% water and about 5% ethanol, about 90% water and about 10% ethanol, about 85% water and about 15% ethanol, about 80% water and about 20% ethanol, about 75% water and about 25% ethanol, about 70% water and about 30% ethanol, about 65% water and about 35% ethanol, about 60% water and about 40% ethanol, about 55% water and about 45% ethanol, or about 50% water and about 50% ethanol by volume. In some embodiments, the extraction solvent comprises about 60% water and about 40% ethanol by volume.

In some embodiments, the weight ratio of herbal parts to extraction solvent ranges from about 1:10 to about 1:2, such as from about 1:10 to 1:3, from about 1:10 to 1:5, from about 1:5 to 1:2, from about 1:5 to 1:3, or from about 1:3 to 1:2. In some embodiments, the weight ratio of herbal parts to extraction solvent is about 1:10. In some embodiments, the weight ratio of herbal parts to extraction solvent is about 1:5. In some embodiments, the weight ratio of herbal parts to extraction solvent is about 1:3.

In some embodiments, the extraction may be carried out at ambient temperature. In some embodiments, the extraction may be carried out at a temperature within the range of from about 15° C. to about 35° C. In some embodiments, the extraction may be carried out at an elevated temperature, such as, for example, from about 35° C. to about 95° C., from about 65° C. to about 95° C., from about 70° C. to about 90° C., or from about 75° C. to about 85° C. In some embodiments, the herbal parts are extracted once. In some embodiments, the herbal parts are extracted multiple times, such as at least two times, at least three times, or more than three times. In some embodiments, aqueous ethanol or water is added to marc of the first extract for further extraction. In some embodiments, aqueous ethanol or water is added to marc of the second extract for further extraction. When the extraction is performed multiple times, each of the individual extracts may be combined and the combined extracts may be concentrated to remove the extraction solvent.

The herbal extracts may be concentrated to remove extraction solvents before further drying. In some embodiments, the herbal extracts may be concentrated using distillation. The herbal extracts may be concentrated in a stainless-steel reactor with agitator, a thin film evaporator, an agitated wiped film evaporator, a calandria distillation unit, a vacuum distillation assembly, or any distillation vessel with vacuum facility. The concentrated extracts may be dried. For example, the concentrated extract may be dried in a tray drier at 90 to 100° C. or spray dried by maintaining an outlet temperature of 90 to 100° C. The herbal extracts may be further powdered in a multi-mill or pulverize to a fine mesh size. The powdered extracts may be sterilized. In some embodiment, heat sterilization may be used. In some embodiments, filtration, radiation, or light may be used. The extracts may be sieved before being packaged.

The herbal extracts of the present disclosure may comprise various active ingredients such as carbohydrates, lipids, proteins, flavonoids, flavones, flavanones, polyphenols, terpenes, saponins, sapogenins, alkaloids, iridoid glycosides, organic acids, minerals, vitamins and many others. The various active ingredients of the herbal extracts may be isolated by selective extraction. In some embodiments, the active ingredients may be isolated and characterized by at least one method chosen from column chromatography, High Pressure Liquid Chromatography (HPLC), Thin Layer Chromatography (TLC), fractional separation, gradient precipitation, crystallization, washing, or derivatization.

In some embodiments, the active ingredients may be identified using High Performance Thin Layer Chromatography (HPTLC), High Pressure Liquid Chromatography (HPLC), Gas Chromatography (GC), Medium Pressure liquid chromatography (MPLC), Column chromatography, liquid chromatography with mass spectrometry (LCMS-MS), gas chromatography with mass spectrometry (LCMSMS), or Inductively coupled plasma mass spectrometry (ICP-MS).

Other than in the examples, or where otherwise indicated, all numbers expressing quantities of ingredients, reaction conditions, analytical measurements and so forth, used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The compositions and methods described herein will be further described by the following non-limiting examples, which are intended to be purely exemplary.

The following examples are intended to illustrate the present disclosure without, however, being limiting in nature. It is understood that the skilled artisan will envision additional embodiments consistent with the disclosure provided herein.

EXAMPLE 1: PREPARING HERBAL EXTRACTS

This example provides an exemplary protocol for preparing various herbal extracts described herein.

FIG. 1 illustrates an exemplary process to produce a *Cardiospermum halicacabum* extract.

First, *Cardiospermum halicacabum* aerial parts were dried and coarsely powdered. The dried and powdered *Cardiospermum halicacabum* aerial parts were charged in a 5000-liter extractor along with 3000 liters of 40% aqueous ethanol and heated for 4-5 hours at 75-85° C. The mixture was cooled to below 60° C. and filtered to recover a first extract.

Next, 3000 liters of 40% aqueous ethanol (v/v) was added to the marc from the first extraction and heated for 4-5 hours at 75-85° C. The mixture was cooled to below 60° C. and filtered to recover a second extract.

Next, 3000 liters of water was added to the marc from the second extraction and heated for 4-5 hours at 85-95° C. The mixture was cooled to below 60° C. and filtered to recover a third extract.

All three extracts were combined and concentrated in a stainless-steel reactor. The combined, concentrated extract was dried in a tray drier at 90-100° C. or spray dried by maintaining an outlet temperature of 90-100° C. The dried extract was further powdered in a multi-mill or pulverizer to a fine mesh size. It was sieved using a sifter to achieve a uniform particle size and blended in an octagonal blender to achieve uniformity. Finally, the product was heat sterilized and sieved again. It was packed in food grade, virgin, double polyethylene bags, and placed in a blue HDPE export worthy drum.

A *Boswellia serrata* extract was produced using the same process described above for the *Cardiospermum halicacabum* extract, except that *Boswellia serrata* gum was used instead of *Cardiospermum halicacabum* aerial parts and the product was precipitated by adding acidified water to the combined, concentrated extract.

A *Curcuma longa* extract was produced using the same process described above for the *Cardiospermum halicacabum* extract, except that *Curcuma longa* rhizomes were used instead of *Cardiospermum halicacabum* aerial parts.

A *Vitex negundo* extract was produced using the same process described above for the *Cardiospermum halicacabum* extract, except that *Vitex negundo* aerial parts were used instead of *Cardiospermum halicacabum* aerial parts.

*Bambusa arundinacea* extract was produced using a different extraction solution. As the first step, *Bambusa arundinacea* shoots are dried. The deposits are carefully removed and powdered. This is treated with boiling water many times, purified, and dried. The rest of the steps are the same as the steps for producing *Cardiospermum halicacabum*, except that water is only used instead of aqueous ethanol.

EXAMPLE 2: PREPARING COMPOSITION A

Figure 2:
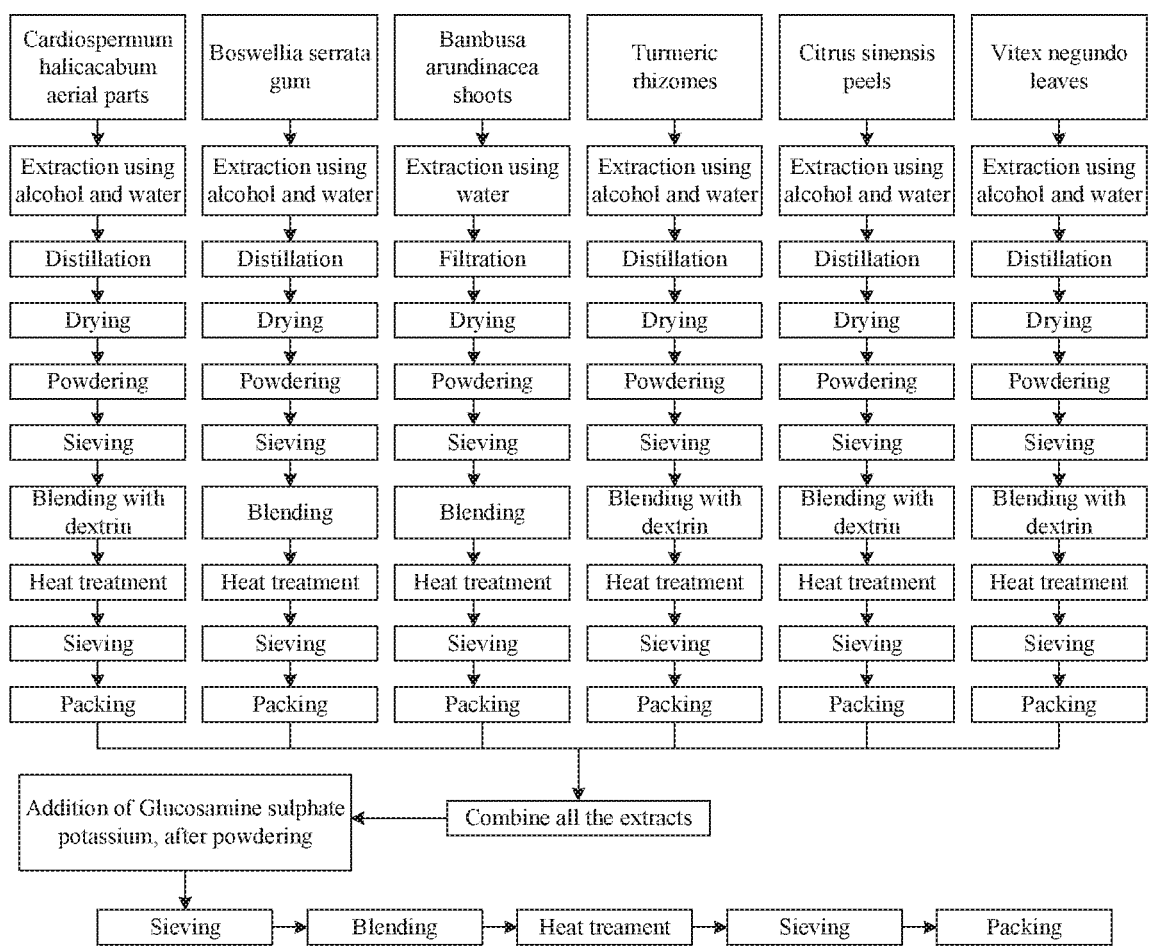
FIG. 2 illustrates an exemplary process for preparing an herbal composition according to the present disclosure.

FIG. 2 illustrates an exemplary process for preparing Composition A. Table 1 shows the ingredients and each of the amounts in Composition A.

TABLE 1

| Composition A | |
|---|---|
| Composition A Ingredients | Amount |
| Glucosamine sulphate potassium | 40% |
| Cardiospermum halicacabum extract | 20.8% |
| Bambusa arundinacea extract | 5% |
| Boswellia serrata extract | 5% |
| Curcuma longa extract | 15% |
| Vitex negundo extract | 10% |
| Citrus sinensis extract | 4.2% |
| Total | 100% |

The following herbal extracts were combined: 1.04 kg of a *Cardiospermum halicacabum* extract, 0.25 kg of a *Bam-* busa arundinacea extract, 0.25 kg of a *Boswellia serrata* extract, 0.75 kg of a *Curcuma longa* extract, 0.5 kg of a *Vitex negundo* extract, and 0.21 kg of a *Citrus sinensis* extract.

The combined extracts were combined with 2 kg of powered glucosamine sulfate potassium. The combined ingredients were sieved using a sifter to achieve a uniform particle size and blended to achieve a uniform mixture. Finally, the product was heat sterilized, sieved again, and packed.

EXAMPLE 3: PREPARING COMPOSITION B

Figure 3:
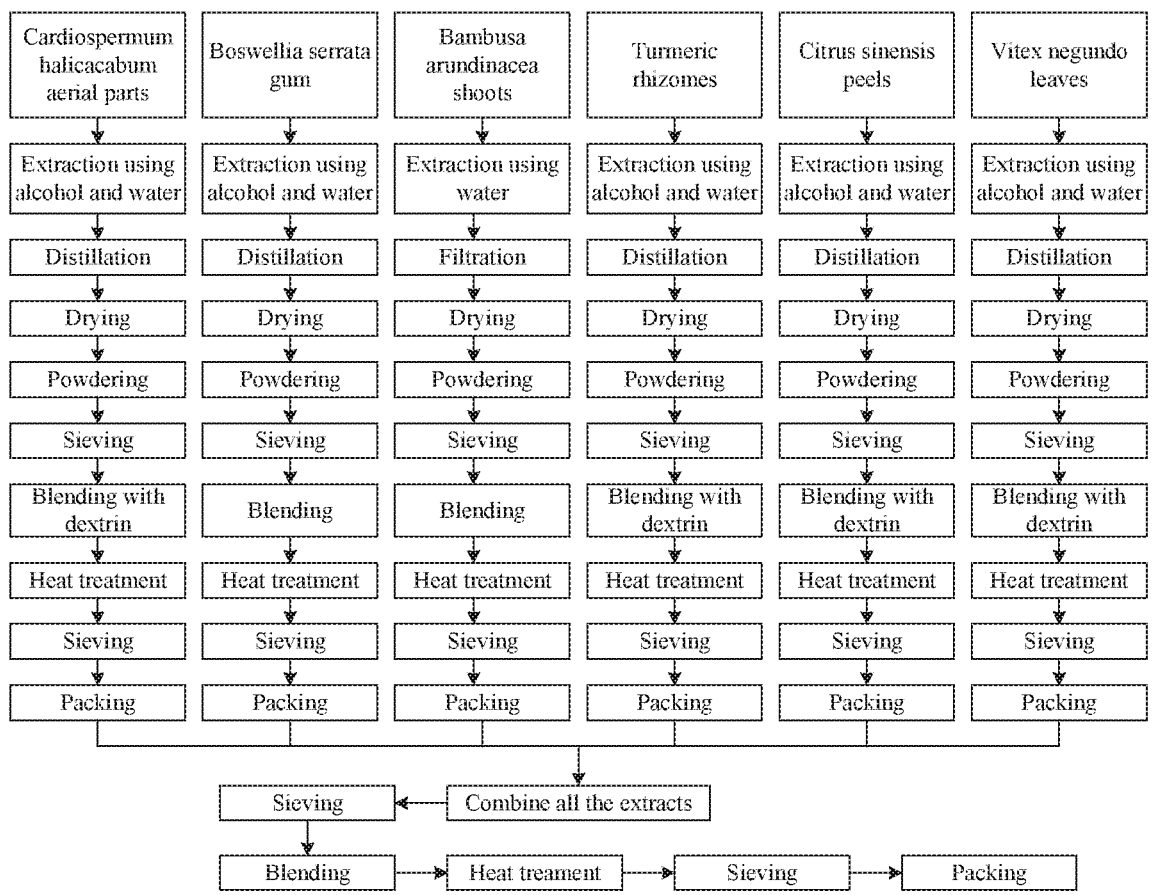
FIG. 3 illustrates an exemplary process for preparing another herbal composition according to the present disclosure.

FIG. 3 illustrates an exemplary process for preparing Composition B. Table 2 shows the ingredients and each of the amounts in Composition B.

TABLE 2

Composition B

| Composition B Ingredients | Amount |
|---|---|
| Cardiospermum halicacabum extract | 37.5% |
| Bambusa arundinacea extract | 5% |
| Boswellia serrata extract | 5% |
| Curcuma longa extract | 15% |
| Vitex negundo extract | 32.5% |
| Citrus sinensis extract | 5% |
| Total | 100% |

The following herbal extracts were combined: 1.875 kg of a *Cardiospermum halicacabum* extract, 0.25 kg of a *Bambusa arundinacea* extract, 0.25 kg of a *Boswellia serrata* extract, 0.75 kg of a *Curcuma longa* extract, 1.625 kg of a *Vitex negundo* extract, and 0.25 kg of a *Citrus sinensis* extract.

The combined extracts were sieved using a sifter to achieve a uniform particle size and blended to achieve a uniform mixture. Finally, the product was heat sterilized, sieved again, and packed.

EXAMPLE 4: IN VIVO STUDIES IN HUMAN SUBJECTS

Composition A from Example 2 and Composition B from Example 3 were prepared and sent for in-vivo testing. Compositions A and B were separately encapsulated. Each capsule contained 500 mg of Composition A or Composition B. The daily dosage was 2 capsules per day in the clinical trial, which makes the daily dosage 1 g. The placebo capsule was filled with only non-active excipients.

Patients and Sample Size

Ambulatory male or female subjects 35-70 years old were recruited for this study. Subjects were screened for study eligibility.

Eligibility criteria included: (a) mild to moderate knee osteoarthritis clinically detected or diagnosed by X-Ray (grade 0, I & II on the Kellgren-Lawrence scale) for primary knee osteoarthritis; (b) otherwise healthy individuals with no clinically significant or relevant abnormalities except for study related condition(s); stable primary hypertensive and newly diagnosed type II diabetic patients with first line medication or without medication were included; (c) willing to refrain from taking ibuprofen, aspirin or other NSAIDS (other than paracetamol as rescue medication), or any other pain reliever (OTC or prescription) during the trial period; (d) female subjects with child bearing potential must be on birth control; female subjects of non-child-bearing potential must have been amenorrhoeic for at least one year or had a hysterectomy, bilateral oophorectomy, or tubectomy; and (e) subjects willing to sign the informed consent and comply with study procedure.

Exclusion criteria for this study included: (a) signs or history of dislocations or quadriceps tendons tear; (b) non-degenerative joint disease or other joint diseases that would interfere with the evaluation of osteoarthritis; (c) acute or congenital illness; history of autoimmune diseases such as rheumatoid arthritis, systemic lupus erythematous, etc.; (d) history of knee or hip joint replacement surgery or any hip or back pain that interferes with ambulation; (e) expecting surgery during the study duration; (f) history of known allergy to NSAIDs or hypersensitivity, allergy or sensitivity to herbal products; (g) taking acetaminophen/paracetamol, ibuprofen, aspirin or other NSAIDs, or any other pain reliever (OTC or prescription), or any natural health product (excluding vitamins) within 7 days prior to the screening; consuming any corticosteroid, indomethacin, glucosamine, or chondroitin within three months prior to the treatment period; intra-articular treatment or injections with corticosteroid or hyaluronic acid within six months of the treatment period; (h) evidence or history of clinically significant condition(s) of hematological, renal, pulmonary, gastrointestinal, cardiovascular, hepatic, or neurological diseases, malignancies or severe thyroid disorders; (i) high alcohol intake (greater than two standard drinks per day) or use of recreational drugs such as cocaine, methamphetamine, marijuana, etc.; (j) history of psychiatric disorder that may impair the ability to provide written informed consent; (k) physical disability that could interfere with the ability to perform the functional performance measures of the protocol; (l) participation in other trials involving investigational or marketed products within 30 days of the screening visit; (m) female subjects who are pregnant, breast feeding, or planning to become pregnant during the study period; and (n) having an HIV positive status.

Patients not meeting the inclusion criteria or meeting the exclusion criteria at the time of screening were not included in the analysis. Eligible subjects were allowed to withdraw from the study at any time.

Trial Design

Eligible subjects who completed the informed consent were randomized to receive Composition A, Composition B, or placebo. As shown in Table 3, Group A had a total of 40 subjects. Subjects in Group A were administered one capsule containing 500 mg of Composition A twice per day (total daily dose of Composition A=1000 mg). Group B had a total of 40 subjects. Subjects in Group B were administered one capsule containing 500 mg of Composition B twice per day (total daily dose of Composition B=1000 mg). The placebo group had a total of 40 subjects. Subjects in the placebo group were administered one placebo capsule twice per day.

TABLE 3

Summary of Subject Demography

| Variable | Statistic | Group A (Composition A) | Group B (Composition B) | Group C (Placebo) |
|---|---|---|---|---|
| Gender | n | 40 | 40 | 40 |
| Female | n (%) | 25 (62.50%) | 23 (57.5%) | 24 (60.0%) |
| Male | n (%) | 15 (37.5%) | 17 (42.5%) | 16 (40.0%) |
| Age at baseline | Mean ± SD | 47.9 ± 8.5 | 50.7 ± 11.1 | 47.7 ± 10.1 |
| | Median | 47 | 53.5 | 46.5 |
| | Min, Max | 35, 68 | 35, 70 | 32, 70 |

Blood and urine samples and an x-ray of the knee were collected at the screening visit and final follow-up visit (day 120±3). Each follow up visit (days 30, 60, 90 and 120±3) involved administration of the supplement, assessments of knee osteoarthritis parameters, and collection of safety and tolerability information.

Primary and Secondary Outcome Measures

The primary endpoint of the study was to compare the improvement in knee osteoarthritis with Compositions A or B treatment compared to placebo control as measured by changes in baseline versus end point scores in the 30 second chair stand test (30SCST). The Western Ontario and McMaster Universities Osteoarthritis Index (WOMAC) was used to assess pain, stiffness and physical function. The knee flexion test was used for range of movements through goniometry. Anteroposterior (AP) and lateral view x-rays of the knee joint were used to confirm diagnosis of osteoarthritis and measure changes in joint width space from baseline to the final visit.

The secondary endpoint of the study was to evaluate the safety and tolerability of Composition A and Composition B by measuring vital signs, laboratory parameters, and adverse events.

Statistical Analysis

All data are expressed as mean (SD) in tables. P values were calculated using a paired t-test to compare time points within the same group, ANOVA to compare groups at the same time point, or ANCOVA using the baseline measurement as a covariant when comparing baseline to visit six across groups. P values <0.05 were considered statistically significant. Missing post-baseline observations were imputed using the last observation carried forward approach.

Results

Thirty-Second Chair Stand Test

The thirty-second chair stand test (30SCST) was used as a clinical measure of the subjects' strength and endurance. The test consists of the subject standing up and sitting down from a chair as many times as possible in 30 seconds while looking straight forward with their arms crossed. The number of times the subject came to a full standing position were counted at baseline (visit 2) and each subsequent visit. At baseline, there was not a statistically significant difference in the 30SCST score between groups (p=0.9873).

Table 4 shows a statistical summary for the 30SCST score from baseline (visit 2, day 1) through visit 6 (day 120±3). As shown in Table 4, subjects in Group A and Group B showed a statistically significant improvement in 30SCST score from baseline to visit six, increasing from 11.08±1.48 to 13.08±1.81 (18%, p<0.0001) and 11.06±1.18 to 12.86±1.69 (16%, p<0.0001), respectively. The placebo group also significantly improved from 11.03±1.55 to 11.88±2.0 (7.7%, p=0.0008).

TABLE 4

Statistical Summary for 30SCST

| Variable | Group A (N = 36) | Group B (N = 34) | Placebo (N = 34) |
| --- | --- | --- | --- |
| 30SCST score at baseline | 11.08(1.481) | 11.06(1.179) | 11.03(1.547) |
| 30SCST score at V3 (Day 30) | 11.58(1.556) | 11.56(1.160) | 11.15(1.617) |
| Diff | 0.5 | 0.5 | 0.12 |
| P Value | <0.0001 | <0.0001 | 0.2541 |
| 30SCST score at baseline | 11.08(1.481) | 11.06(1.179) | 11.03(1.547) |
| 30SCST score at V4 (Day 60) | 11.75(1.645) | 11.94(1.434) | 11.32(1.736) |
| Diff | 0.67 | 0.88 | 0.29 |
| P Value | <0.0001 | <0.0001 | 0.0960 |
| 30SCST score at baseline | 11.08(1.481) | 11.06(1.179) | 11.03(1.547) |

TABLE 4-continued

Statistical Summary for 30SCST

| Variable | Group A (N = 36) | Group B (N = 34) | Placebo (N = 34) |
| --- | --- | --- | --- |
| 30SCST score at V5 (Day 90) | 12.39(1.591) | 12.31(1.587) | 11.47(1.727) |
| Diff | 1.31 | 1.25 | 0.44 |
| P Value | <0.0001 | <0.0001 | <0.0299 |
| 30SCST score at baseline | 11.08(1.481) | 11.06(1.179) | 11.03(1.547) |
| 30SCST score at V6 (Day 120) | 13.08(1.811) | 12.86(1.691) | 11.88(1.996) |
| Diff | 2 | 1.80 | 0.85 |
| P Value | <0.0001 | <0.0001 | 0.0008 |

Table 5 shows the overall ANOVA P values (P Value$^a$) for the 30SCST scores across all three groups at baseline and each subsequent visit. Table 5 also shows the Unpaired T Test P values for comparisons between the Group A and Group B 30SCST scores (P Value$^{aa}$), the Group A and placebo 30SCST scores (P Value$^{ac}$), and the Group B and placebo 30SCST scores (P Value$^{ab}$) at baseline and each subsequent visit.

TABLE 5

Overall ANOVA and Unpaired T Test P Values for 30SCST

| Variable | P Value$^a$ (ANOVA Overall) | P Value$^{aa}$ (A-B) | P Value$^{ac}$ (A-P) | P Value$^{ab}$ (B-P) |
| --- | --- | --- | --- | --- |
| 30SCST score at baseline | 0.9873 | 0.9971 | 0.9861 | 0.9959 |
| 30SCST score at V3 (Day 30) | 0.3831 | 0.9973 | 0.4272 | 0.4782 |
| 30SCST score at V4 (Day 60) | 0.2737 | 0.8732 | 0.5119 | 0.2585 |
| 30SCST score at V5 (Day 90) | 0.0392 | 0.9798 | 0.0538 | 0.0897 |
| 30SCST score at V6 (Day 120) | 0.0181 | 0.8650 | 0.0200 | 0.0777 |

Table 6 shows the overall ANCOVA P values (P Value$^b$) for the 30SCST scores across all three groups at visits 3 through 6 with the score at baseline (visit 2) as a covariate. Table 6 also shows the ANCOVA P values for comparisons between the Group A and Group B 30SCST scores (P Value$^{ba}$), the Group A and placebo 30SCST scores (P Value$^{bb}$), and the Group B and placebo 30SCST scores (P Value$^{bc}$) at visits 3 through 6 with the score at baseline (visit 2) as a covariate. After adjusting for baseline score as a covariate, there was a statistically significant difference in 30SCST score between baseline and visit 6 (day 120±3) across all three groups (p=0.0007), with both Group A and Group B showing a statistically significant increase compared to the placebo group (p=0.0009 and p=0.0088, respectively).

TABLE 6

ANCOVA P Values for 30SCST with Baseline as Covariate

| Variable | P Value$^b$ (ANCOVA Overall) | P Value$^{ba}$ (A-B) | P Value$^{bb}$ (A-P) | P Value$^{bc}$ (B-P) |
| --- | --- | --- | --- | --- |
| 30SCST score at V3 (Day 30) | 0.0072 | >0.99 | 0.0158 | 0.0181 |
| 30SCST score at V4 (Day 60) | 0.0163 | 0.5340 | 0.1551 | 0.0129 |
| 30SCST score at V5 (Day 90) | 0.0009 | 0.9751 | 0.0020 | 0.0046 |
| 30SCST score at V6 (Day 120) | 0.0007 | 0.7893 | 0.0009 | 0.0088 |

Assessment of Pain, Stiffness, and Physical Function

WOMAC is a self-administered health status measure consisting of 24 questions that describe the subjects' pain, stiffness, and physical functions. It was developed to specifically quantify the symptoms of knee osteoarthritis for the purpose of evaluating outcomes following a clinical trial. Subjects were asked to complete the WOMAC questions at the baseline visit and each subsequent visit.

Table 7 shows a statistical summary for the WOMAC A (pain) score from baseline (visit 2, day 1) through visit 6 (day 120±3). An improvement from baseline is indicated by a reduction in WOMAC score. The WOMAC A (pain) score significantly decreased in all groups from baseline to visit 6: from 5.94±2.59 to 1.58±2.27 (73% reduction, p<0.0001) in Group A; from 5.94±2.22 to 1.74±1.40 (71% reduction, p<0.0001) in Group B; and from 4.41±1.88 to 2.24±1.21 (49% reduction, p<0.0001) in the placebo group.

TABLE 7

Statistica Summary for WOMAC A (Pain)

| Variable | Group A (N = 36) | Group B (N = 34) | Placebo (N = 34) |
|---|---|---|---|
| WOMAC A score at baseline | 5.94(2.585) | 5.94(2.215) | 4.41(1.877) |
| WOMAC A score at V3 (Day 30) | 4.56(2.602) | 5.03(1.962) | 4.29(2.834) |
| Diff | 1.38 | 0.91 | 1.12 |
| P Value | <0.0001 | 0.0009 | 0.6798 |
| WOMAC A score at baseline | 5.94(2.585) | 5.94(2.215) | 4.41(1.877) |
| WOMAC A score at V4 (Day 60) | 3.69(2.352) | 3.82(1.660) | 3.59(2.217) |
| Diff | 2.25 | 2.12 | 0.82 |
| P Value | <0.0001 | <0.0001 | <0.052 |
| WOMAC A score at baseline | 5.94(2.585) | 5.94(2.215) | 4.41(1.877) |
| WOMAC A score at V5 (Day 90) | 2.67(2.414) | 2.82(1.696) | 3.15(1.778) |
| Diff | 3.28 | 3.12 | 1.26 |
| P Value | <0.0001 | <0.0001 | 0.0002 |
| WOMAC A score at baseline | 5.94(2.585) | 5.94(2.215) | 4.41(1.877) |
| WOMAC A score at V6 (Day 120) | 1.58(2.273) | 1.74(1.399) | 2.24(1.208) |
| Diff | 4.36 | 4.20 | 2.17 |
| P Value | <0.0001 | <0.0001 | <0.0001 |

Table 8 shows the overall ANOVA P values (P Value$^a$) for the WOMAC A scores across all three groups at baseline and each subsequent visit. Table 8 also shows the Unpaired T Test P values for comparisons between the Group A and Group B WOMAC A scores (P Value$^{aa}$), the Group A and placebo WOMAC A scores (P Value$^{ac}$), and the Group B and placebo WOMAC A scores (P Value$^{ab}$) at baseline and each subsequent visit.

TABLE 8

ANOVA and Unpaired T Test P Values for WOMAC A (Pain)

| Variable | P Value$^a$ (ANOVA Overall) | P Value$^{aa}$ (A-B) | P Value$^{ac}$ (A-P) | P Value$^{ab}$ (B-P) |
|---|---|---|---|---|
| WOMAC A score at baseline | 0.0065 | >0.99 | 0.0147 | 0.0167 |
| WOMAC A score at V3 (Day 30) | 0.4706 | 0.7075 | 0.8997 | 0.4472 |
| WOMAC A score at V4 (Day 60) | 0.8989 | 0.9644 | 0.9757 | 0.8895 |
| WOMAC A score at V5 (Day 90) | 0.5948 | 0.9424 | 0.5752 | 0.7828 |
| WOMAC A score at V6 (Day 120) | 0.2549 | 0.9263 | 0.2506 | 0.4504 |

Table 9 shows the overall ANCOVA P values (P Value$^b$) for the WOMAC A score across all three groups at visits 3 through 6 with the score at baseline (visit 2) as a covariate. Table 9 also shows the ANCOVA P Values for comparisons between the Group A and Group B WOMAC A scores (P Value$^{ba}$), the Group A and placebo WOMAC A scores (P Value$^{bb}$), and the Group B and placebo WOMAC A scores (P Value$^{bc}$) at visits 3 through 6 with the score at baseline (visit 2) as a covariate. After adjusting for baseline score as a covariate, there was a statistically significant difference in WOMAC A score between baseline and visit 6 (day 120±3) across all three groups (p=0.0036), with both Group A and Group B showing a statistically significant improvement compared to the placebo group (p=0.0048 and p=0.0176, respectively).

TABLE 9

ANCOVA P Values for WOMAC A (Pain) with Baseline as Covariate

| Variable | P Value$^b$ (ANCOVA Overall) | P Value$^{ba}$ (A-B) | P Value$^{bb}$ (A-P) | P Value$^{bc}$ (B-P) |
|---|---|---|---|---|
| WOMAC A score at V3 (Day 30) | 0.0409 | 0.4385 | 0.0311 | 0.3614 |
| WOMAC A score at V4 (Day 60) | 0.0749 | 0.9352 | 0.0798 | 0.1685 |
| WOMAC A score at V5 (Day 90) | 0.0223 | 0.9242 | 0.0259 | 0.0685 |
| WOMAC A score at V6 (Day 120) | 0.0036 | 0.9051 | 0.0048 | 0.0176 |

Table 10 shows a statistical summary for WOMAC B (stiffness) score from baseline (visit 2, day 1) through visit 6 (day 120±3). The WOMAC B score was significantly different between groups at baseline and significantly decreased in all groups from baseline to visit 6: Group A decreased from 0.50±0.81 to 0.17±0.45 (66% reduction, p=0.0007); Group B decreased from 1.03±1.09 to 0.29±0.68 (71.8% reduction, p<0.0001); and the placebo group decreased from 1.09±0.93 to 0.56±0.79 (48.6% reduction, p<0.0001).

TABLE 10

Statistical Summary for WOMAC B (Stiffness)

| Variable | Group A (n = 36) | Group B (n = 34) | Placebo (n = 34) |
|---|---|---|---|
| WOMAC B score at baseline | 0.50(0.811) | 1.03(1.087) | 1.09(0.933) |
| WOMAC B score at V3 (Day 30) | 0.50(0.811) | 1.03(1.087) | 1.09(0.933) |
| Diff | — | — | — |
| P Value* | — | — | — |
| WOMAC B score at baseline | 0.50(0.811) | 1.03(1.087) | 1.09(0.933) |
| WOMAC B score at V4 (Day 60) | 0.42(0.732) | 0.76(0.855) | 0.82(0.716) |
| Diff | 0.08 | 0.27 | 0.27 |
| P Value* | 0.0831 | 0.0016 | 0.0016 |
| WOMAC B score at baseline | 0.50(0.811) | 1.03(1.087) | 1.09(0.933) |
| WOMAC B score at V5 (Day 90) | 0.22(0.485) | 0.44(0.894) | 0.65(0.774) |
| Diff | 0.28 | 0.59 | 0.44 |
| P Value* | 0.0026 | <0.0001 | <0.0001 |
| WOMAC B score at baseline | 0.50(0.811) | 1.03(1.087) | 1.09(0.933) |
| WOMAC B score at V6 (Day 120) | 0.17(0.447) | 0.29(0.676) | 0.56(0.786) |
| Diff | 0.33 | 0.74 | 0.53 |
| P Value* | 0.0007 | <0.0001 | <0.0001 |

Table 11 shows the overall ANOVA P values (P Value$^a$) for the WOMAC B (stiffness) scores across all three groups at baseline and each subsequent visit. Table 11 also shows the Unpaired T Test P values for comparisons between the Group A and Group B WOMAC B scores (P Value$^{aa}$), the Group A and placebo WOMAC B scores (P Value$^{ac}$), and the Group B and placebo WOMAC B scores (P Value$^{ab}$) at baseline and each subsequent visit.

TABLE 11

ANOVA and Unpaired T Test P Values for WOMAC B (Stiffness)

| Variable | P Value$^a$ (ANOVA Overall) | P Value$^{aa}$ (A-B) | P Value$^{ac}$ (A-P) | P Value$^{ab}$ (B-P) |
|---|---|---|---|---|
| WOMAC B score at baseline | 0.0190 | 0.0554 | 0.0290 | 0.9645 |
| WOMAC A score at V3 (Day 30) | 0.0190 | 0.0554 | 0.0290 | 0.9645 |
| WOMAC A score at V4 (Day 60) | 0.0607 | 0.1465 | 0.0742 | 0.9467 |
| WOMAC A score at V5 (Day 90) | 0.0577 | 0.4280 | 0.0451 | 0.4816 |
| WOMAC A score at V6 (Day 120) | 0.0406 | 0.6902 | 0.0343 | 0.2164 |

Table 12 shows the overall ANCOVA P values (P Value$^b$) for the WOMAC B (stiffness) score across all three groups at visits 3 through 6 with the score at baseline (visit 2) as a covariate. Table 12 also shows the ANCOVA P Values for comparisons between the Group A and Group B WOMAC B scores (P Value$^{ba}$), the Group A and placebo WOMAC B scores (P Value$^{bb}$), and the Group B and placebo WOMAC B scores (P Value$^{bc}$) at visits 3 through 6 with the score at baseline (visit 2) as a covariate. Although there was a reduction over time in all groups, there was not a statistically significant difference in WOMAC B score between baseline and visit 6 (day 120±3) across all three groups (p=0.0992) after adjusting for baseline score as a covariate. However, as can be seen in Table 12, there was a decreasing trend observed in the ANCOVA p values over time (p=0.8436, p=0.3365, p=0.0992 at visits four, five, and six, respectively), suggesting that a longer duration may be necessary to observe a statistically significant effect.

TABLE 12

ANCOVA P Values for WOMAC B (Stiffness) with Baseline as Covariate

| Variable | P Value$^b$ (ANCOVA Overall) | P Value$^{ba}$ (A-B) | P Value$^{bb}$ (A-P) | P Value$^{bc}$ (B-P) |
|---|---|---|---|---|
| WOMAC A score at V3 (Day 30) | 0.8436 | 0.8332 | 0.9246 | 0.9784 |
| WOMAC A score at V4 (Day 60) | 0.8436 | 0.8332 | 0.9246 | 0.9784 |
| WOMAC A score at V5 (Day 90) | 0.3365 | 0.7015 | 0.7896 | 0.3043 |
| WOMAC A score at V6 (Day 120) | 0.0992 | 0.4383 | 0.6387 | 0.0821 |

Table 13 shows a statistical summary for the WOMAC C (physical function) score from baseline (visit 2, day 1) through visit 6 (day 120±3). The WOMAC C score was significantly different across groups at baseline, with Group B having a higher score compared to Group A and the placebo group. The WOMAC C score of all groups decreased from baseline to visit 6: Group A decreased from 13.08±8.41 to 3.53±5.13 (73% reduction, p<0.0001), Group B decreased from 15.74±8.78 to 4.85±3.53 (69% reduction, p<0.0001), and the placebo group decreased from 12.21±6.27 to 5.65±2.55 (54% reduction, p<0.0001).

TABLE 13

Statistical Summary for WOMAC C (Physical Function)

| Variable | Group A (n = 36) | Group B (n = 34) | Placebo (n = 34) |
|---|---|---|---|
| WOMAC C score at baseline | 13.08(8.412) | 15.74(8.781) | 12.21(6.266) |
| WOMAC C score at V3 (Day 30) | 11.31(7.270) | 14.29(8.259) | 10.62(5.152) |
| Diff | 1.77 | 1.45 | 1.59 |
| P Value | <0.0001 | <0.0001 | <0.0001 |
| WOMAC C score at baseline | 13.08(8.412) | 15.74(8.781) | 12.21(6.266) |
| WOMAC C score at V4 (Day 60) | 9.22(6.339) | 11.35(7.298) | 10.06(4.690) |
| Diff | 3.86 | 4.39 | 2.15 |
| P Value | <0.0001 | <0.0001 | <0.0001 |
| WOMAC C score at baseline | 13.08(8.412) | 15.74(8.781) | 12.21(6.266) |
| WOMAC C score at V5 (Day 90) | 5.36(5.494) | 6.53(4.826) | 6.53(3.067) |
| Diff | 7.72 | 9.21 | 5.68 |
| P Value | <0.0001 | <0.0001 | <0.0001 |
| WOMAC C score at baseline | 13.08(8.412) | 15.74(8.781) | 12.21(6.266) |
| WOMAC C score at V6 (Day 120) | 3.53(5.130) | 4.85(3.526) | 5.65(2.545) |
| Diff | 9.55 | 10.89 | 6.56 |
| P Value | <0.0001 | <0.0001 | <0.0001 |

Table 14 shows the overall ANOVA P values (P Value$^a$) for the WOMAC C (physical function) scores across all three groups at baseline and each subsequent visit. Table 14 also shows the Unpaired T Test P Values for comparisons between the Group A and Group B WOMAC C scores (P Value$^{aa}$), the Group A and placebo WOMAC C scores (P Value$^{ac}$), and the Group B and placebo WOMAC C scores (P Value$^{ab}$) at baseline and each subsequent visit.

TABLE 14

ANOVA and Unpaired T Test P Values for WOMAC C (Physical Function)

| Variable | P Value$^a$ (ANOVA Overall) | P Value$^{aa}$ (A-B) | P Value$^{ac}$ (A-P) | P Value$^{ab}$ (B-P) |
|---|---|---|---|---|
| WOMAC C score at baseline | 0.1639 | 0.3436 | 0.8883 | 0.1619 |
| WOMAC A score at V3 (Day 30) | 0.0757 | 0.1814 | 0.9117 | 0.0833 |
| WOMAC A score at V4 (Day 60) | 0.3564 | 0.3266 | 0.8396 | 0.6668 |
| WOMAC A score at V5 (Day 90) | 0.4704 | 0.5395 | 0.5395 | >0.99 |
| WOMAC A score at V6 (Day 120) | 0.0768 | 0.3361 | 0.0654 | 0.6809 |

Table 15 shows the overall ANCOVA P values for the WOMAC C (physical function) score across all three groups at visits 3 through 6 with the score at baseline (visit 2) as a covariate. Table 15 also shows the ANCOVA P values for comparisons between the Group A and Group B WOMAC C scores (P Value$^{ba}$), the Group A and placebo WOMAC C scores (P Value$^{bb}$), and the Group B and placebo WOMAC C scores (P Value$^{bc}$) at visits 3 through 6 with the score at baseline (visit 2) as a covariate.

After adjusting for baseline score as a covariate, there was not a statistically significant difference in WOMAC C score between baseline and visit 3 (day 30±3) across all three groups (p=0.1080). However, as can be seen in Table 15, there was a statistically significant difference in WOMAC C score between baseline and visit 6 (day 120±3) across all three groups (p=0.0122), with Group A showing a statistically significant improvement compared to the placebo group (p=0.0109). This suggests that physical function capabilities of subjects improved gradually over time.

TABLE 15

ANCOVA P Values for WOMAC C with Baseline as Covariate

| Variable | P Value[b] (ANCOVA Overall) | P Value[ba] (A-B) | P Value[bb] (A-P) | P-Value[bc] (B-P) |
|---|---|---|---|---|
| WOMAC A score at V3 (Day 30) | 0.1080 | 0.1246 | 0.9744 | 0.2027 |
| WOMAC A score at V4 (Day 60) | 0.0545 | 0.9217 | 0.0589 | 0.1537 |
| WOMAC A score at V5 (Day 90) | 0.1209 | 0.9901 | 0.1471 | 0.2093 |
| WOMAC A score at V6 (Day 120) | 0.0122 | 0.7162 | 0.0109 | 0.0945 |

Knee Flexion

The range of knee flexion was measured using goniometry while the subject was lying down. A goniometer was placed on the lateral aspect of the leg to be assessed. As the subject flexed their knee, the difference between the beginning and end angle measurement was noted.

Table 16 shows a statistical summary for knee flexion range of motion as measured by goniometry from baseline (visit 2, day 1) through visit 6 (day 120±3). All groups showed a statistically significant improvement in range of knee flexion from baseline to visit 6. Group A improved from 121.11±7.66° at baseline to 128.89±8.38° at visit 6 (6.4%, p<0.0001); Group B improved from 113.68±6.89° at baseline to 122.50±6.99° at visit 6 (7.7%, p<0.0001); and the placebo group improved from 115.00±6.40° at baseline to 119.12±6.91° at visit 6 (3.6%, p<0.0001).

TABLE 16

Statistical Summary for Knee Flexion

| Variable | Group A (n = 36) | Group B (n = 34) | Placebo (n = 34) |
|---|---|---|---|
| Knee Flexion at baseline | 121.11(7.664) | 113.68(6.887) | 115.00(6.396) |
| Knee Flexion at V3 (Day 30) | 122.36(8.493) | 115.88(6.089) | 115.44(6.321) |
| Diff | 1.25 | 2.21 | 0.44 |
| P Value | 0.0049 | <0.0001 | 0.0831 |
| Knee Flexion at baseline | 121.11(7.664) | 113.68(6.887) | 115.00(6.396) |
| Knee Flexion at V4 (Day 60) | 123.75(8.483) | 116.03(6.370) | 115.74(6.171) |
| Diff | 2.64 | 2.35 | 0.74 |
| P Value | 0.0230 | <0.0001 | 0.0230 |
| Knee Flexion at baseline | 121.11(7.664) | 113.68(6.887) | 115.00(6.396) |
| Knee Flexion at V5 (Day 90) | 127.22(8.819) | 118.68(5.547) | 117.21(6.536) |
| Diff | 6.11 | 5.00 | 2.21 |
| P Value | <0.0001 | <0.0001 | 0.0005 |
| Knee Flexion at baseline | 121.11(7.664) | 113.68(6.887) | 115.00(6.396) |
| Knee Flexion at V6 (Day 120) | 128.89(8.376) | 122.50(6.990) | 119.12(6.905) |
| Diff | 7.78 | 8.82 | 4.12 |
| P Value | <0.0001 | <0.0001 | <0.0001 |

Table 17 shows the overall ANOVA P values (P Value[a]) for the knee flexion measurements across all three groups at baseline and each subsequent visit. Table 17 also shows the Unpaired T Test P values for comparisons between the Group A and Group B knee flexion measurements (P Value[aa]), the Group A and placebo knee flexion measurements (P Value[ac]), and the Group B and placebo knee flexion measurements (P-Value[ab]) at baseline and each subsequent visit.

TABLE 17

ANOVA and Unpaired T Test P Values for Knee Flexion

| Variable | P Value[a] (ANOVA Overall) | P Value[aa] (A-B) | P Value[ac] (A-P) | P-Value[ab] (B-P) |
|---|---|---|---|---|
| Knee Flexion at baseline | <0.0001 | <0.0001 | 0.0012 | 0.7174 |
| WOMAC A score at V3 (Day 30) | <0.0001 | 0.0007 | 0.0003 | 0.9643 |
| WOMAC A score at V4 (Day 60) | <0.0001 | <0.0001 | <0.0001 | 0.9841 |
| WOMAC A score at V5 (Day 90) | <0.0001 | 0.0016 | <0.0001 | 0.6733 |
| WOMAC A score at V6 (Day 120) | <0.0001 | 0.0016 | <0.0001 | 0.1539 |

Table 18 shows the overall ANCOVA P values (P Value[b]) for the knee flexion score across all three groups at visits 3 through 6 with the score at baseline (visit 2) as a covariate. Table 18 also shows the ANCOVA P values for comparisons between the Group A and Group B knee flexions scores (P Value[ba]), the Group A and placebo knee flexion scores (P Value[bb]), and the Group B and placebo knee flexion scores (P Value[bc]) at visits 3 through 6 with the score at baseline (visit 2) as a covariate. After adjusting for baseline as a covariate, there was a statistically significant difference in degree of knee flexion between baseline and visit 6 (day 120±3) across all three groups (p=0.0001), with both Group A and Group B showing a statistically significant increase compared to the placebo group (p=0.0005 and p=0.0008, respectively).

TABLE 18

ANCOVA P Values for Knee Flexion with Baseline as Covariate

| Variable | P Value[b] (ANCOVA Overall) | P Value[ba] (A-B) | P Value[bb] (A-P) | P-Value[bc] (B-P) |
|---|---|---|---|---|
| WOMAC A score at V3 (Day 30) | 0.0110 | 0.5652 | 0.1607 | 0.0088 |

TABLE 18-continued

ANCOVA P Values for Knee Flexion with Baseline as Covariate

| Variable | P Value$^b$ (ANCOVA Overall) | P Value$^{ba}$ (A-B) | P Value$^{bb}$ (A-P) | P-Value$^{bc}$ (B-P) |
|---|---|---|---|---|
| WOMAC A score at V4 (Day 60) | 0.0045 | 0.5393 | 0.0043 | 0.0654 |
| WOMAC A score at V5 (Day 90) | <0.0001 | 0.0807 | <0.0001 | 0.0270 |
| WOMAC A score at V6 (Day 120) | 0.0001 | 0.9572 | 0.0005 | 0.0008 |

X-Ray of Knee Joint

At baseline (visit 2, day 1) and final follow-up (visit 6, day 120±3), x-rays of the anteroposterior and lateral views of the knee were collected to measure minimum joint space width of the medial compartment of the tibiofemoral joint.

Table 19 shows a statistical summary for radiographic minimum knee joint space width. All groups showed statistically significant improvement in knee joint space width from baseline to visit six, with Group A improving from 1.58±0.32 mm to 1.95±0.32 mm (23%, p<0.0001), Group B improving from 1.54±0.47 mm to 1.92±0.54 mm (25%, p=0.0001), and the placebo group improving from 1.52±0.31 mm to 1.69±0.41 mm (11%, p=0.0013).

TABLE 19

Statistical Summary for Knee Joint Width

| Variable | Group A (n = 36) | Group B (n = 34) | Placebo (n = 34) |
|---|---|---|---|
| Knee Joint Width at baseline | 1.58(0.315) | 1.54(0.471) | 1.52(0.310) |
| Knee Joint Width at V6 (Day 120) | 1.95(0.320) | 1.92(0.543) | 1.69(0.408) |
| Diff | 0.37 | 0.38 | 0.17 |
| P Value | <0.0001 | 0.0001 | 0.0013 |

Table 20 shows the overall ANOVA P values (P Value$^a$) for radiographic knee joint space width measurements across all three groups at baseline and visit 6. Table 20 also shows the Unpaired T Test P values for comparisons between the Group A and Group B radiographic knee joint space width (P Value$^{aa}$), the Group A and placebo radiographic knee joint space width (P Value$^{ac}$), and the Group B and placebo radiographic knee joint space width (P Value$^{ab}$) at baseline and visit 6.

TABLE 20

ANOVA and Unpaired T Test P Values for Knee Joint Width

| Variable | P Value$^a$ (ANOVA Overall) | P Value$^{aa}$ (A-B) | P Value$^{ac}$ (A-P) | P Value$^{ab}$ (B-P) |
|---|---|---|---|---|
| Knee Joint Width at baseline | 0.8033 | 0.9300 | 0.7867 | 0.9536 |
| Knee Joint Width at V6 (Day 120) | 0.0253 | 0.9470 | 0.0325 | 0.0750 |

Table 21 shows the overall ANCOVA P values (P Value$^b$) for radiographic minimum knee joint space width measurements across all three groups at visit 6 with the score at baseline (visit 2) as covariate. Table 21 also shows the ANCOVA P values for comparisons between the Group A and Group B knee joint width measurements (P Value$^{ba}$), the Group A and placebo knee joint width measurements (P Value$^{bb}$), and the Group B and placebo knee joint width measurements (P Value$^{bc}$) at visit 6 with the score at baseline (visit 2) as covariate. After adjusting for baseline as a covariate, there was a statistically significant difference in radiographic knee joint space width between baseline and visit 6 (day 120±3) across all three groups (p=0.0036), with both Group A and Group B showing a statistically significant improvement compared to the placebo group (p=0.0229 and p=0.0339, respectively).

TABLE 21

ANCOVA P Values for Knee Joint Width with Baseline as Covariate

| Variable | P Value$^b$ (ANCOVA Overall) | P Value$^{ba}$ (A-B) | P Value$^{bb}$ (A-P) | P-Value$^{bc}$ (B-P) |
|---|---|---|---|---|
| Knee Joint Width at V6 (day 120) | 0.0036 | 0.9923 | 0.0229 | 0.0339 |

Blood Tests

At baseline (visit 2, day 1) and visit 6 (day 120±3), approximately 5-8 mL of blood was collected for clinical laboratory evaluation of markers associated with osteoarthritis. The blood was tested for serum calcium, alkaline phosphatase (ALP), and c-reactive protein (CRP). The level of all three of these substances in serum has been associated with the presence or severity of knee osteoarthritis. Serum calcium shows an inverse relationship (Li et al., 2016), while CRP and ALP increase with osteoarthritis progression and the associated inflammation (Gogebakan, Izmirli, Okuyan, & Atac, 2016; Pearle et al., 2007).

Table 22 shows a statistical summary of serum calcium levels. Serum calcium levels increased in all three arms between baseline readings and visit six, including a statistically significant increase in Group A (p=0.0015) and Group B (p=0.0056), but there was no statistically significant increase in the placebo group (p=0.3599).

TABLE 22

Statistical Summary for Serum Calcium

| Variable | Group A (n = 36) | Group B (n = 34) | Placebo (n = 34) | P Value$^a$ (ANOVA Overall) | P Value$^b$ (ANCOVA Overall) |
|---|---|---|---|---|---|
| Calcium at baseline | 9.41 (0.514) | 9.46 (0.445) | 9.50 (0.556) | 0.7885 | 0.2321 |
| Calcium at V6 (Day 120) | 9.82 (0.499) | 9.79 (0.539) | 9.62 (0.506) | 0.2315 | |

TABLE 22-continued

Statistical Summary for Serum Calcium

| Variable | Group A (n = 36) | Group B (n = 34) | Placebo (n = 34) | P Value[a] (ANOVA Overall) | P Value[b] (ANCOVA Overall) |
|---|---|---|---|---|---|
| Diff | 0.41 | 0.33 | 0.12 | | |
| P value | 0.0015 | 0.0056 | 0.3599 | | |

Adverse Events and Safety

The safety of the study supplements was measured by recording vital signs, results of a physical examination, clinical laboratory tests (including comprehensive metabolic profiling and hematology parameters), and any adverse events that occurred while taking the supplements. All parameters were normal and did not significantly change during the study. There were no serious adverse events observed in any of the subjects during the course of this study. Minor adverse events were observed in 19 subjects. The minor events included gastritis, fever, abdominal bloating, rhinitis, drowsiness, and vomiting. These events were evenly distributed throughout the three arms, including five in group A, six in group B, and eight in the placebo control group. Most of these adverse events were self-limiting and subsided without any intervention. Study physicians prescribed concomitant medication to some of the subjects for few days.

What is claimed is:

1. A method of improving or maintaining joint health or increasing joint space in a subject, comprising administering to a subject an effective amount of an herbal composition, wherein the herbal composition comprises:
   from about 29% to about 35% of a concentrated *Vitex negundo* extract, by weight relative to the total weight of the herbal composition, concentrated in at least one iridoid glycoside or a pharmaceutically acceptable salt or solvate thereof;
   from about 34% to about 40% of a concentrated *Cardiospermum halicacabum* extract, by weight relative to the total weight of the herbal composition, concentrated in at least one hydroxy flavone derivative or a pharmaceutically acceptable salt or solvate thereof;
   from about 4% to about 8% of a concentrated *Bambusa arundinacea* extract, by weight relative to the total weight of the herbal composition, concentrated in silica;
   from about 2% to about 6% of a concentrated *Citrus sinensis* extract, by weight relative to the total weight of the herbal composition, concentrated in at least one bioflavonoid or a pharmaceutically acceptable salt or solvate thereof;
   from about 2% to about 6% of a concentrated *Boswellia serrata* extract, by weight relative to the total weight of the herbal composition, concentrated in at least one pentacyclic triterpenic acid or a pharmaceutically acceptable salt or solvate thereof; and
   from about 12% to about 18% of a concentrated *Curcuma longa* extract, by weight relative to the total weight of the herbal composition, concentrated in at least one water soluble saponin glycoside or a pharmaceutically acceptable salt or solvate thereof;
   wherein the combination of the amount of the composition comprising the concentrated *Vitex negundo* extract, the concentrated *Cardiospermum halicacabum* extract, the concentrated *Bambusa arundinacea* extract, the concentrated *Citrus sinensis* extract, the concentrated *Boswellia serrata* extract, and the concentrated *Curcuma longa* extract is effective to improve or maintain joint health or increase joint space in the subject.

2. The method according to claim 1, wherein the ratio of the concentrated *Vitex negundo* extract to the concentrated *Cardiospermum halicacabum* extract is from about 1:1 to about 1:1.251:2.5.

3. The method according to claim 1, wherein the composition comprises about 32.5% of the *Vitex negundo* extract, about 37.5% of the *Cardiospermum halicacabum* extract, about 5% of the *Bambusa arundinacea* extract, about 5% of the *Citrus sinensis* extract, about 5% of the *Boswellia serrata* extract, and about 15% of the *Curcuma longa* extract, by weight relative to the total weight of the composition.

4. The method according to claim 1, wherein each extract is standardized to a powder comprised of particles of substantially uniform size before being mixed with other extracts.

5. The method according to claim 2, wherein the *Vitex negundo* extract is an extract from *Vitex negundo* aerial parts,
   the *Cardiospermum halicacabum* extract is an extract from *Cardiospermum halicacabum* aerial parts,
   the *Bambusa arundinacea* extract is an extract from *Bambusa arundinacea* shoots,
   the *Citrus sinensis* extract is an extract of *Citrus sinensis* peels,
   the *Boswellia serrata* extract is an extract of *Boswellia serrata* gum, and
   the *Curcuma longa* extract is an extract of *Curcuma longa* rhizomes.

6. The method according to claim 3, wherein the amount of the composition comprising the *Vitex negundo* extract, the *Cardiospermum halicacabum* extract, the *Bambusa arundinacea* extract, the *Citrus sinensis* extract, the *Boswellia serrata* extract, and the *Curcuma longa* extract is effective to improve or maintain joint health or reduce, alleviate, and/or slow the progression of at least one symptom of in the subject as shown by improvement in the subject's joint health as measured by changes in baseline versus end point scores in:
   a 30 second chair stand test (30SCST);
   a Western Ontario and McMaster Universities Osteoarthritis Index (WOMAC) score (WOMAC A Pain), (WOMAC B Stiffness), and/or (WOMAC C Physical function);
   range of motion in knee flexion; and/or
   radiographic minimum joint space width.

7. The method according to claim 6, wherein the composition is effective to increase joint space in a subject as measured by changes in baseline versus endpoint scores in radiographic minimum joint space.

8. The method according to claim 4, wherein the *Vitex negundo* extract, the *Cardiospermum halicacabum* extract, the *Citrus sinensis* extract, the *Boswellia serrata* gum extract, and the *Curcuma longa* extract are from one or more extractions with aqueous alcohol.

9. The method according to claim 8, wherein the alcohol comprises methanol, ethanol, or combinations thereof.

10. The method according to claim 5, wherein the composition further comprises at least one pharmaceutically acceptable excipient and/or antioxidant.

11. A method of improving or maintaining joint health or increasing joint space in a subject, comprising administering to a subject an effective amount of an herbal composition, wherein the herbal composition comprises:
    from about 8% to about 12% of a concentrated *Vitex negundo* extract, by weight relative to the total weight of the herbal composition, concentrated in at least one iridoid glycoside or a pharmaceutically acceptable salt or solvate thereof;
    from about 18% to about 22% of a concentrated *Cardiospermum halicacabum* extract, by weight relative to the total weight of the herbal composition, concentrated in at least one hydroxy flavone derivative or a pharmaceutically acceptable salt or solvate thereof;
    from about 4% to about 8% of a concentrated *Bambusa arundinacea* extract, by weight relative to the total weight of the herbal composition, concentrated in silica;
    from about 3% to about 6% of a concentrated *Citrus sinensis* extract, by weight relative to the total weight of the herbal composition, concentrated in at least one bioflavonoid or a pharmaceutically acceptable salt or solvate thereof;
    from about 4% to about 6% of a concentrated *Boswellia serrata* extract, by weight relative to the total weight of the herbal composition, concentrated in at least one pentacyclic triterpenic acid or a pharmaceutically acceptable salt or solvate thereof;
    from about 12% to about 18% of a concentrated *Curcuma longa* extract, by weight relative to the total weight of the herbal composition, enriched concentrated in at least one water soluble saponin glycoside or a pharmaceutically acceptable salt or solvate thereof; and
    from about 37% to about 42% of Glucosamine or a pharmaceutically acceptable salt or solvate thereof;
    wherein the amount of the composition comprising the concentrated *Vitex negundo* extract, the concentrated *Cardiospermum halicacabum* extract, the concentrated *Bambusa arundinacea* extract, the concentrated *Citrus sinensis* extract, the concentrated *Boswellia serrata* extract, the concentrated *Curcuma longa* extract, and the Glucosamine is effective to improve or maintain joint health or increase joint space in the subject.

12. The method according to claim 11, wherein the ratio of the concentrated *Vitex negundo* extract to the concentrated *Cardiospermum halicacabum* extract is from about 1:1.5 to about 1:2.5.

13. The method according to claim 11, wherein the composition comprises about 10% of the *Vitex negundo* extract, about 20.8° 20% of the *Cardiospermum halicacabum* extract, about 5% of the *Bambusa arundinacea* extract, about 4.2% 4% of the *Citrus sinensis* extract, about 5% of the *Boswellia serrata* extract, about 15% of the *Curcuma longa* extract, and about 40% of the Glucosamine, by weight relative to the total weight of the composition.

14. The method according to claim 11, wherein each extract is standardized to a powder comprised of particles of substantially uniform size before being mixed with other extracts.

15. The method according to claim 12, wherein the *Vitex negundo* extract is an extract from *Vitex negundo* aerial parts,
    the *Cardiospermum halicacabum* extract is an extract from *Cardiospermum halicacabum* aerial parts,
    the *Bambusa arundinacea* extract is an extract from *Bambusa arundinacea* shoots,
    the *Citrus sinensis* extract is an extract of *Citrus sinensis* peels,
    the *Boswellia serrata* extract is an extract of *Boswellia serrata* gum, and
    the *Curcuma longa* extract is an extract of *Curcuma longa* rhizomes.

16. The method according to claim 13, wherein the amount of the composition comprising the *Vitex negundo* extract, the *Cardiospermum halicacabum* extract, the *Bambusa arundinacea* extract, the *Citrus sinensis* extract, the *Boswellia serrata* extract, the *Curcuma longa* extract, and the Glucosamine is effective to improve or maintain joint health or reduce, alleviate, and/or slow the progression of at least one symptom of in the subject as shown by improvement in the subject's joint health as measured by changes in baseline versus end point scores in:
    a 30 second chair stand test (30SCST);
    a Western Ontario and McMaster Universities Osteoarthritis Index (WOMAC) score (WOMAC A Pain), (WOMAC B Stiffness), and/or (WOMAC C Physical function);
    range of motion in knee flexion; and/or
    radiographic minimum joint space width.

17. The method according to claim 11, wherein the *Vitex negundo* extract, the *Cardiospermum halicacabum* extract, the *Citrus sinensis* extract, the *Boswellia serrata* gum extract, and the *Curcuma longa* extract are from one or more extractions with aqueous alcohol.

18. The method according to claim 17, wherein the alcohol comprises methanol, ethanol, or combinations thereof.

19. The method according to claim 15, wherein the composition further comprises at least one pharmaceutically acceptable excipient and/or antioxidant.

20. The method according to claim 16, wherein the composition is effective to increase joint space in a subject as measured by changes in baseline versus endpoint scores in radiographic minimum joint space.

21. The method according to claim 1, wherein the at least one iridoid glycoside is a compound according to Formula (I):

or a pharmaceutically acceptable salt of solvate thereof; and wherein the at least one flavone derivative is a compound according to Formula (II):

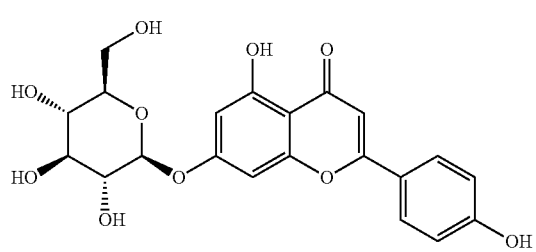

or a pharmaceutically acceptable salt of solvate thereof.

22. The method according to claim 11, wherein the at least one iridoid glycoside is a compound according to Formula (I) or a pharmaceutically acceptable salt of solvate thereof; and wherein the at least one flavone derivative is a compound according to Formula (II) or a pharmaceutically acceptable salt of solvate thereof.

23. A method of improving or maintaining joint health or increasing joint space in a subject, comprising
orally administering to a human subject an herbal composition in an effective amount of about 0.1 g to about 4 g per day for at least about 30 days, or
topically administering to a human subject an herbal composition in an effective amount of about 0.1 g to about 10 g per day for at least about 30 days,
wherein the herbal composition consists essentially of:
from about 29% to about 35% of a concentrated *Vitex negundo* extract, by weight relative to the total weight of the herbal composition, concentrated in at least one iridoid glycoside or a pharmaceutically acceptable salt or solvate thereof;
from about 34% to about 40% of a concentrated *Cardiospermum halicacabum* extract, by weight relative to the total weight of the herbal composition, concentrated in at least one hydroxy flavone derivative or a pharmaceutically acceptable salt or solvate thereof;
from about 4% to about 8% of a concentrated *Bambusa arundinacea* extract, by weight relative to the total weight of the herbal composition, concentrated in silica;
from about 2% to about 6% of a concentrated *Citrus sinensis* extract, by weight relative to the total weight of the herbal composition, concentrated in at least one bioflavonoid or a pharmaceutically acceptable salt or solvate thereof;
from about 2% to about 6% of a concentrated *Boswellia serrata* extract, by weight relative to the total weight of the herbal composition, concentrated in at least one pentacyclic triterpenic acid or a pharmaceutically acceptable salt or solvate thereof; and
from about 12% to about 18% of a concentrated *Curcuma longa* extract, by weight relative to the total weight of the herbal composition, concentrated in at least one water soluble saponin glycoside or a pharmaceutically acceptable salt or solvate thereof.

24. The method according to claim 23, wherein the composition further comprises at least one pharmaceutically acceptable excipient and/or antioxidant.

25. The method according to claim 24, wherein the ratio of the concentrated *Vitex negundo* extract to the concentrated *Cardiospermum halicacabum* extract is from about 1:1 to about 1:2.5.

26. The method according to claim 24, wherein the composition comprises about 32.5% of the *Vitex negundo* extract, about 37.5% of the *Cardiospermum halicacabum* extract, about 5% of the *Bambusa arundinacea* extract, about 5% of the *Citrus sinensis* extract, about 5% of the *Boswellia serrata* extract, and about 15% of the *Curcuma longa* extract, by weight relative to the total weight of the composition.

27. The method according to claim 26, wherein the *Bambusa arundinacea* extract comprises about 50% to about 75% by weight silica.

28. The method according to claim 23, wherein the at least one iridoid glycoside is a compound according to Formula (I) or a pharmaceutically acceptable salt of solvate thereof; and wherein the at least one flavone derivative is a compound according to Formula (II) or a pharmaceutically acceptable salt of solvate thereof.

29. A method of improving or maintaining joint health or increasing joint space in a subject, comprising
orally administering to a human subject an herbal composition in an effective amount of about 0.1 g to about 4 g per day for at least about 30 days, or
topically administering to a human subject an herbal composition in an effective amount of about 0.1 g to about 10 g per day for at least about 30 days,
wherein the herbal composition consists essentially of:
from about 8% to about 12% of a concentrated *Vitex negundo* extract, by weight relative to the total weight of the herbal composition, concentrated in at least one iridoid glycoside or a pharmaceutically acceptable salt or solvate thereof;
from about 18% to about 22% of a concentrated *Cardiospermum halicacabum* extract, by weight relative to the total weight of the herbal composition, concentrated in at least one hydroxy flavone derivative or a pharmaceutically acceptable salt or solvate thereof;
from about 4% to about 8% of a concentrated *Bambusa arundinacea* extract, by weight relative to the total weight of the herbal composition, concentrated in silica;
from about 3% to about 6% of a concentrated *Citrus sinensis* extract, by weight relative to the total weight of the herbal composition, concentrated in at least one bioflavonoid or a pharmaceutically acceptable salt or solvate thereof;
from about 4% to about 6% of a concentrated *Boswellia serrata* extract, by weight relative to the total weight of the herbal composition, concentrated in at least one pentacyclic triterpenic acid or a pharmaceutically acceptable salt or solvate thereof;
from about 12% to about 18% of a concentrated *Curcuma longa* extract, by weight relative to the total weight of the herbal composition, concentrated in at least one water soluble saponin glycoside or a pharmaceutically acceptable salt or solvate thereof; and
from about 37% to about 42% of Glucosamine or a pharmaceutically acceptable salt or solvate thereof.

30. The method according to claim 29, wherein the composition further comprises at least one pharmaceutically acceptable excipient and/or antioxidant.

31. The method according to claim 30, wherein the ratio of the concentrated *Vitex negundo* extract to the concentrated *Cardiospermum halicacabum* extract is from about 1:1 to about 1:2.5.

32. The method according to claim 30, wherein the composition comprises about 10% of the *Vitex negundo* extract, about 20% of the *Cardiospermum halicacabum* extract, about 5% of the *Bambusa arundinacea* extract, about 4% of the *Citrus sinensis* extract, about 5% of the *Boswellia serrata* extract, about 15% of the *Curcuma longa* extract, and about 40% of the Glucosamine, by weight relative to the total weight of the composition.

33. The method according to claim 32, wherein the *Bambusa arundinacea* extract comprises about 50% to about 75% by weight silica.

34. The method according to claim 29, wherein the at least one iridoid glycoside is a compound according to Formula (I) or a pharmaceutically acceptable salt of solvate thereof; and wherein the at least one flavone derivative is a compound according to Formula (II) or a pharmaceutically acceptable salt of solvate thereof.

\* \* \* \* \*

UNITED STATES PATENT AND TRADEMARK OFFICE
CERTIFICATE OF CORRECTION

Page 1 of 2

PATENT NO. : 11,364,255 B2
APPLICATION NO. : 16/946721
DATED : June 21, 2022
INVENTOR(S) : Krishna Rajendran It is certified that error appears in the above-identified patent and that said Letters Patent is hereby corrected as shown below:

In the Claims

Claim 2, Column 44, Lines 18-19, "from about 1:1 to about 1:1.251:2.5" should read --from about 1:1 to about 1:2.5--.

Claim 6, Column 44, Line 51, "at least one symptom of in the" should read --at least one symptom in the--.

Claim 11, Column 45, Line 39, "enriched concentrated" should read --concentrated--.

Claim 13, Column 45, Line 58, "about 20.8° 20%" should read --about 20%--.

Claim 13, Column 45, Line 60, "about 4.2% 4%" should read --about 4%--.

Claim 16, Column 46, Lines 21-22, "at least one symptom of in the" should read --at least one symptom in the--.

Claim 21, Column 46, Line 66, "salt of solvate thereof" should read --salt or solvate thereof--.

Claim 21, Column 47, Line 17, "salt of solvate thereof" should read --salt or solvate thereof--.

Claim 22, Column 47, Line 20, "salt of solvate thereof" should read --salt or solvate thereof--.

Claim 22, Column 47, Line 24, "salt of solvate thereof" should read --salt or solvate thereof--.

Claim 28, Column 48, Line 19, "salt of solvate thereof" should read --salt or solvate thereof--.

Claim 28, Column 48, Line 23, "salt of solvate thereof" should read --salt or solvate thereof--.

Signed and Sealed this
Twenty-seventh Day of February, 2024

Katherine Kelly Vidal
*Director of the United States Patent and Trademark Office*

Claim 34, Column 49, Line 19, "salt of solvate thereof" should read --salt or solvate thereof--.

Claim 34, Column 49, Line 22, "salt of solvate thereof" should read --salt or solvate thereof--.